United States Patent
Fanton et al.

(10) Patent No.: US 10,258,322 B2
(45) Date of Patent: Apr. 16, 2019

(54) METHOD AND APPARATUS FOR PASSING SUTURE

(71) Applicant: SP Surgical Inc., Portola Valley, CA (US)

(72) Inventors: Gary S. Fanton, Portola Valley, CA (US); John F. Krumme, Woodside, CA (US); Scott H. Heneveld, Whitmore, CA (US); Matthew B. Newell, Redwood City, CA (US); Luke W. Clauson, Redwood City, CA (US)

(73) Assignee: Maruho Medical, Inc., Reno, NV (US)

( * ) Notice: Subject to any disclaimer, the term of this patent is extended or adjusted under 35 U.S.C. 154(b) by 168 days.

(21) Appl. No.: 14/255,945

(22) Filed: Apr. 17, 2014

(65) Prior Publication Data

US 2014/0316443 A1    Oct. 23, 2014

Related U.S. Application Data

(60) Provisional application No. 61/812,805, filed on Apr. 17, 2013.

(51) Int. Cl.
*A61B 17/04*    (2006.01)
*A61B 17/06*    (2006.01)

(52) U.S. Cl.
CPC ...... *A61B 17/0469* (2013.01); *A61B 17/0482* (2013.01); *A61B 17/06004* (2013.01); *A61B 2017/06052* (2013.01)

(58) Field of Classification Search
CPC .......... A61B 17/06004; A61B 17/0482; A61B 17/0469; A61B 17/29; A61B 2017/06052; A61B 2017/2926; A61B 2017/2927; A61B 2017/2929; A61B 2017/2932; A61B 2017/2933; A61B 2017/2934; A61B 2017/2936; A61B 2017/2937; A61B 2017/2939; A61B 2017/294; A61B 2017/2941; A61B 2017/2944; A61B 2017/2947
USPC ........................................................ 606/144
See application file for complete search history.

(56) References Cited

U.S. PATENT DOCUMENTS

| | | | |
|---|---|---|---|
| 1,822,330 | A | 9/1931 | Ainslie |
| 4,935,027 | A | 6/1990 | Yoon |
| 5,172,700 | A | 12/1992 | Bencini et al. |
| 5,254,126 | A | 10/1993 | Filipi et al. |
| 5,632,751 | A | 5/1997 | Piraka |
| 5,769,857 | A | 6/1998 | Reztzov et al. |
| 5,797,927 | A * | 8/1998 | Yoon ................. A61B 17/0469 606/139 |

(Continued)

FOREIGN PATENT DOCUMENTS

| | | |
|---|---|---|
| DE | 91 09 097 | 9/1991 |
| DE | 297 05 871 | 6/1997 |

(Continued)

*Primary Examiner* — Katrina Stransky
*Assistant Examiner* — Martin T Ton
(74) *Attorney, Agent, or Firm* — Levine Bagade Han LLP

(57) ABSTRACT

A device is disclosed that can pierce and hold tissue and then pass suture through tissue. The device can have a shuttle that can removably attach to a suture and jaws that can be rotatably opened and closed with respect to each other. A method for using the device to repeatedly pass the suture through the tissue without removing the suture or device from the target site is also disclosed.

20 Claims, 31 Drawing Sheets

(56) References Cited

U.S. PATENT DOCUMENTS

| | | |
|---|---|---|
| 5,876,412 A | 3/1999 | Piraka |
| 5,908,428 A | 6/1999 | Scirica et al. |
| 6,010,523 A * | 1/2000 | Sabin ............... A61B 10/06 600/562 |
| 6,056,771 A | 5/2000 | Proto |
| 6,511,489 B2 | 1/2003 | Field et al. |
| 6,533,795 B1 | 3/2003 | Tran et al. |
| 7,166,116 B2 | 1/2007 | Lizardi et al. |
| 7,232,446 B1 | 6/2007 | Farris |
| 7,377,926 B2 | 5/2008 | Topper et al. |
| 7,431,724 B2 | 10/2008 | Manetakis et al. |
| 7,572,265 B2 | 8/2009 | Stone et al. |
| 7,972,344 B2 | 7/2011 | Murray et al. |
| 8,177,796 B2 | 5/2012 | Akyruz et al. |
| 2003/0023250 A1 | 1/2003 | Watschke et al. |
| 2003/0181910 A1 | 9/2003 | Dycus et al. |
| 2005/0273131 A1 | 12/2005 | Shluzas et al. |
| 2005/0288690 A1 | 12/2005 | Bourque et al. |
| 2008/0027468 A1 | 1/2008 | Fenton et al. |
| 2009/0012538 A1 * | 1/2009 | Saliman ............. A61B 17/0491 606/145 |
| 2009/0306684 A1 * | 12/2009 | Stone ................ A61B 17/0625 606/145 |
| 2010/0023027 A1 | 1/2010 | Watschke et al. |
| 2011/0152891 A1 | 6/2011 | McLawhorn et al. |
| 2011/0152892 A1 | 6/2011 | Saliman et al. |

FOREIGN PATENT DOCUMENTS

| | | |
|---|---|---|
| JP | 09-224947 | 9/1997 |
| WO | WO 1995/009566 | 4/1995 |
| WO | WO 1998/003116 | 1/1998 |
| WO | WO 2014/172589 | 10/2014 |

\* cited by examiner

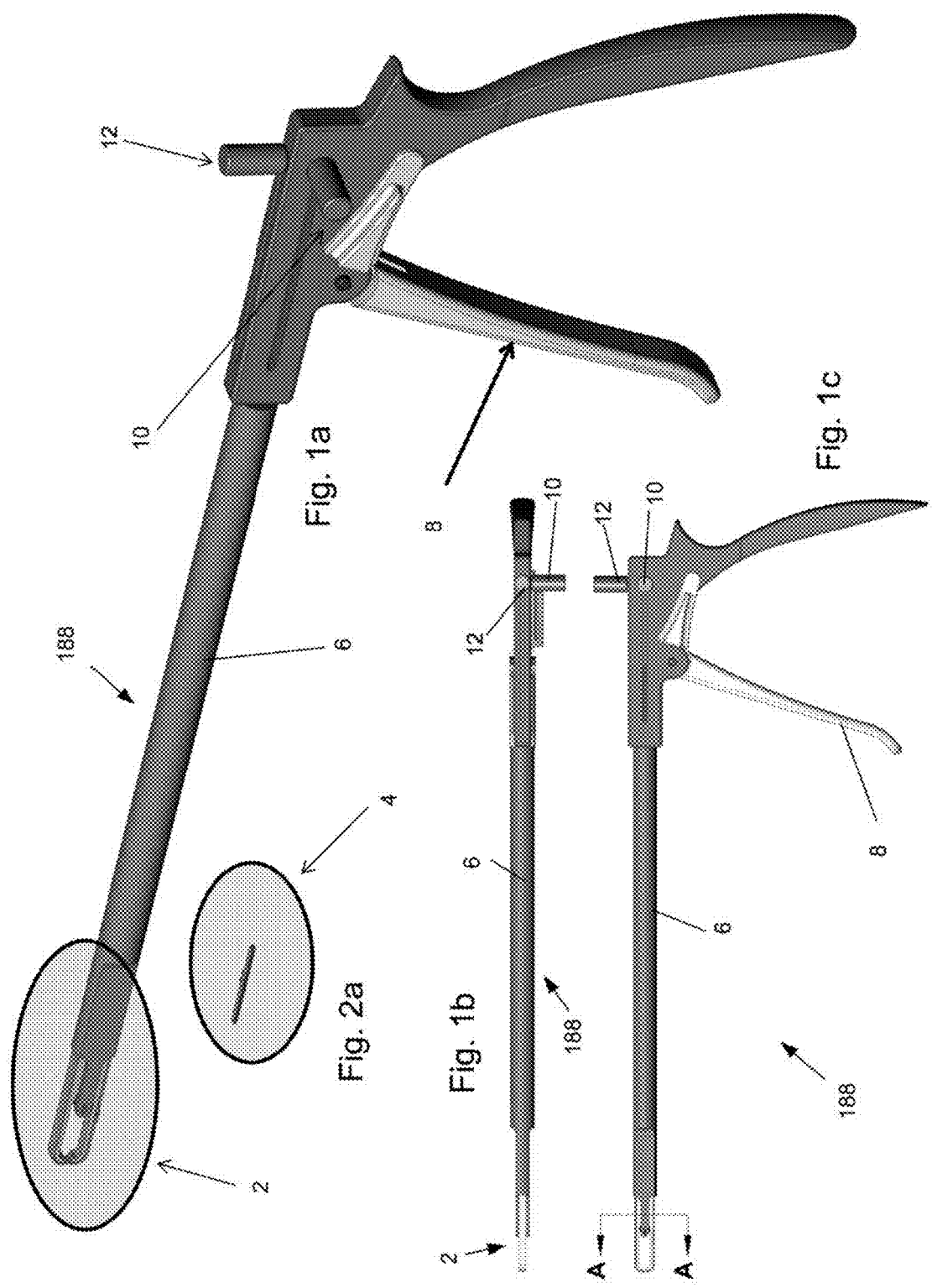

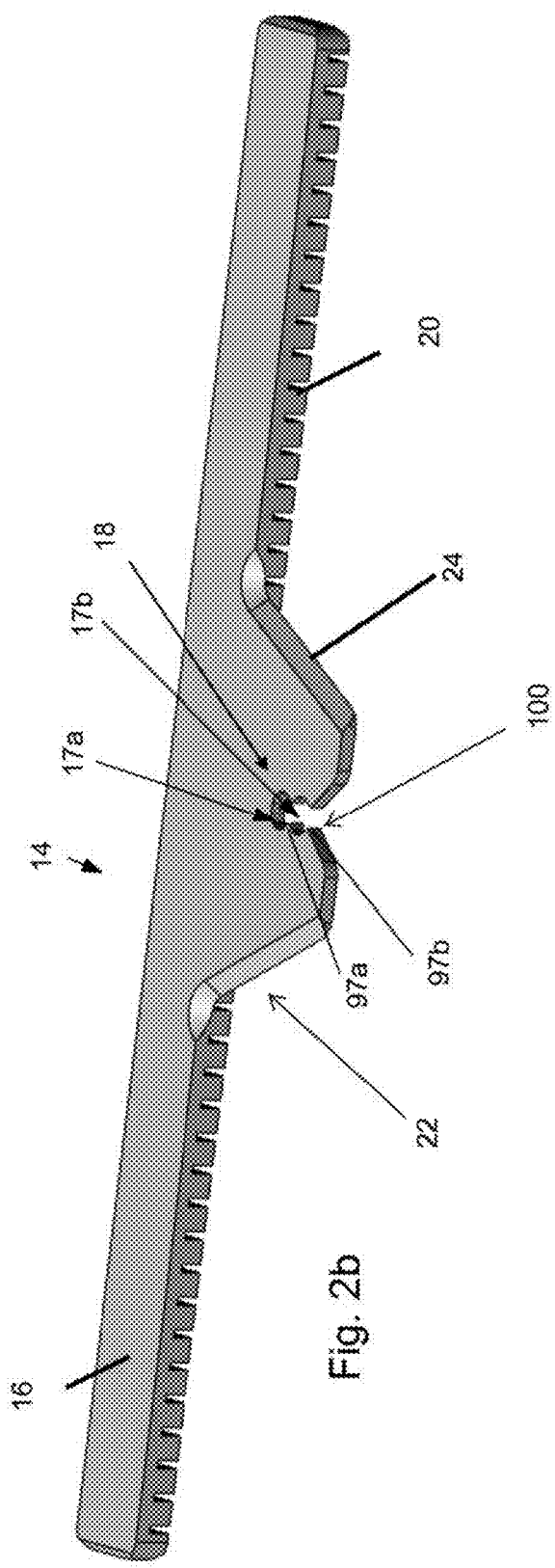
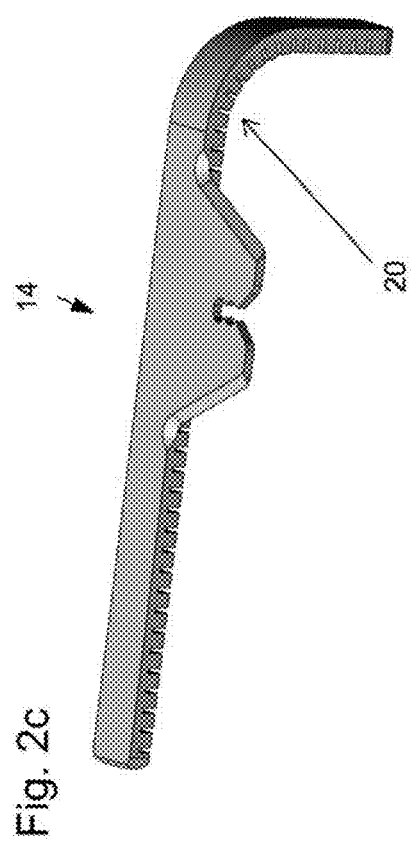
Fig. 2b
Fig. 2c

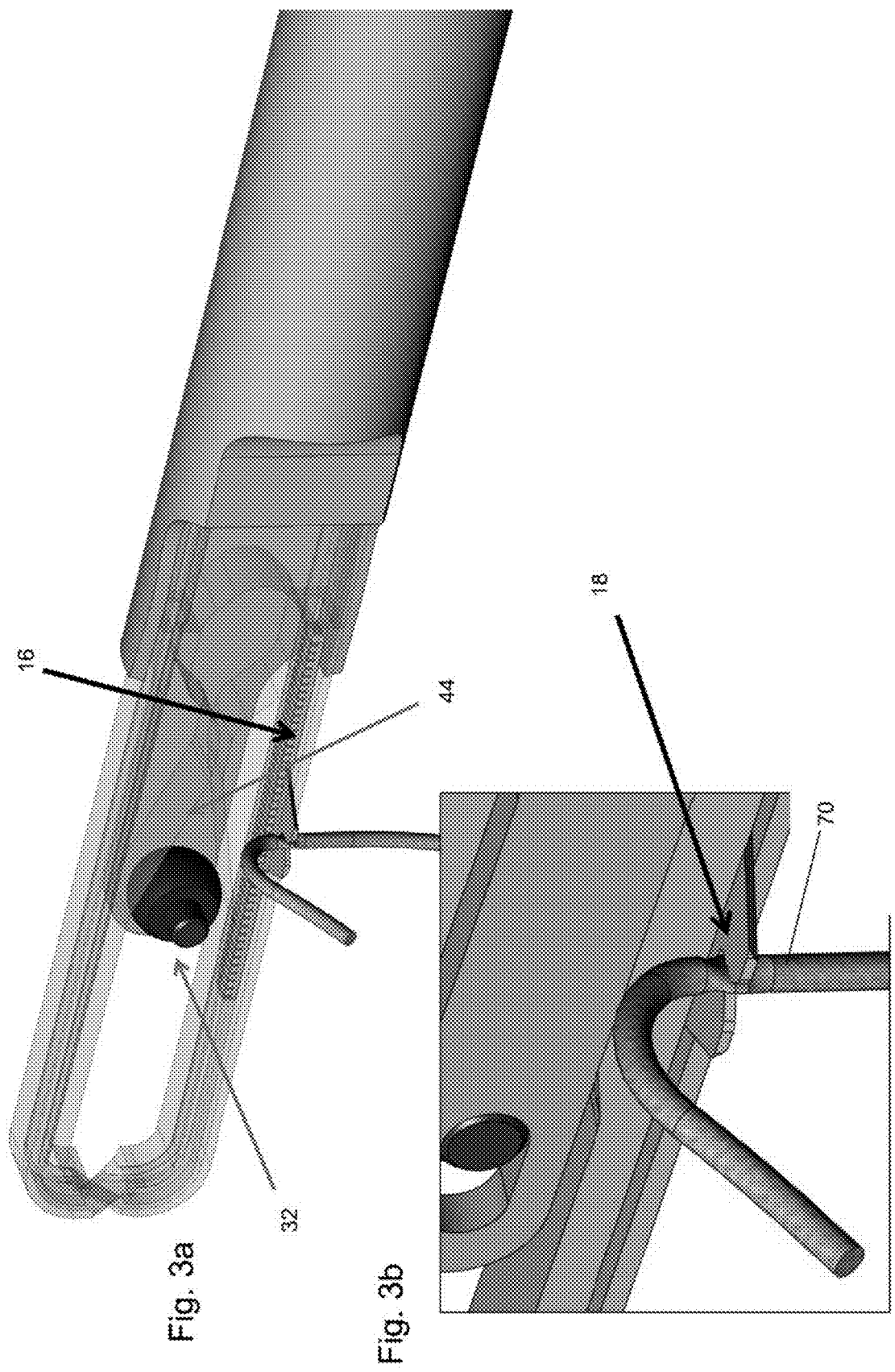

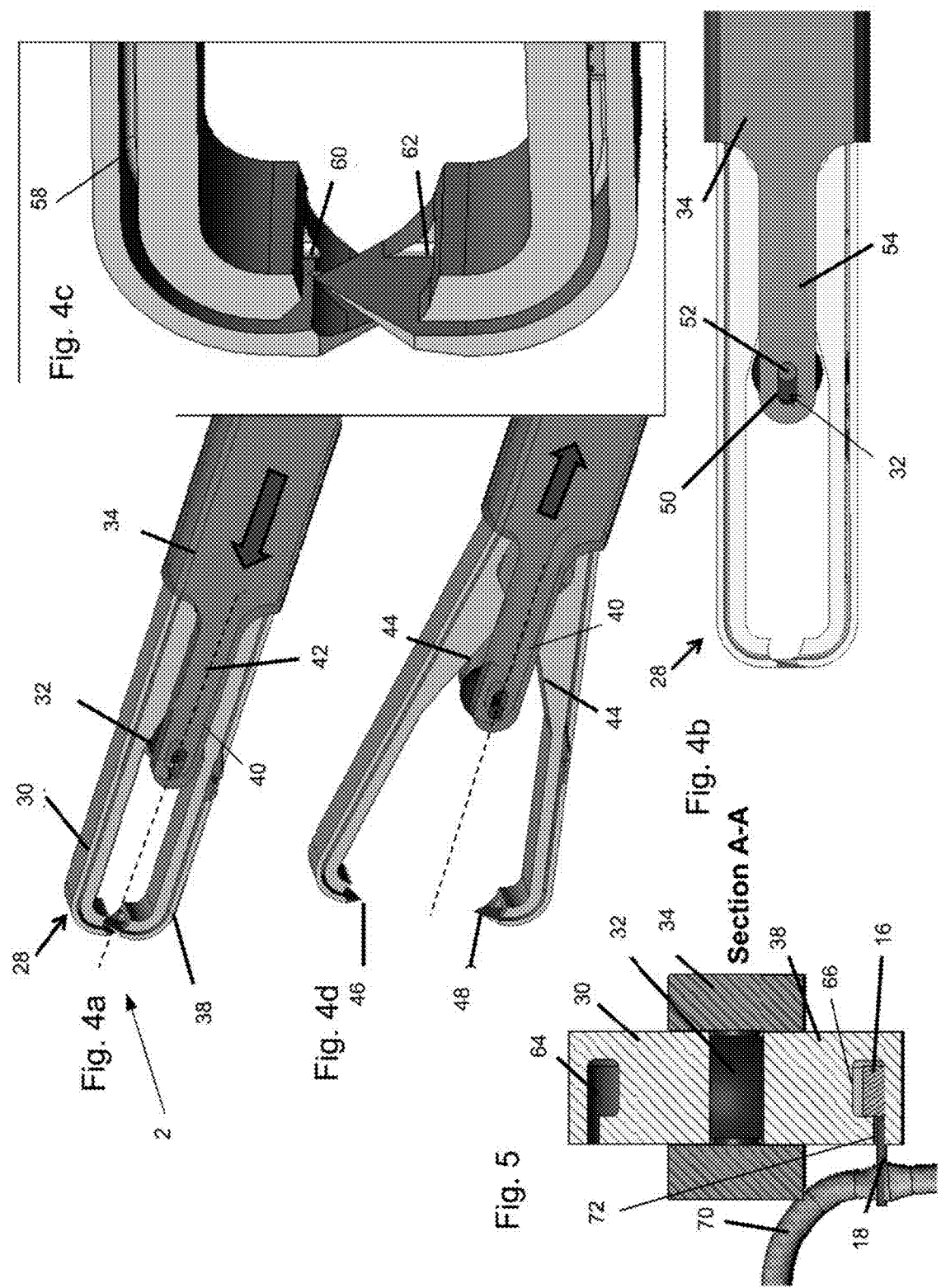

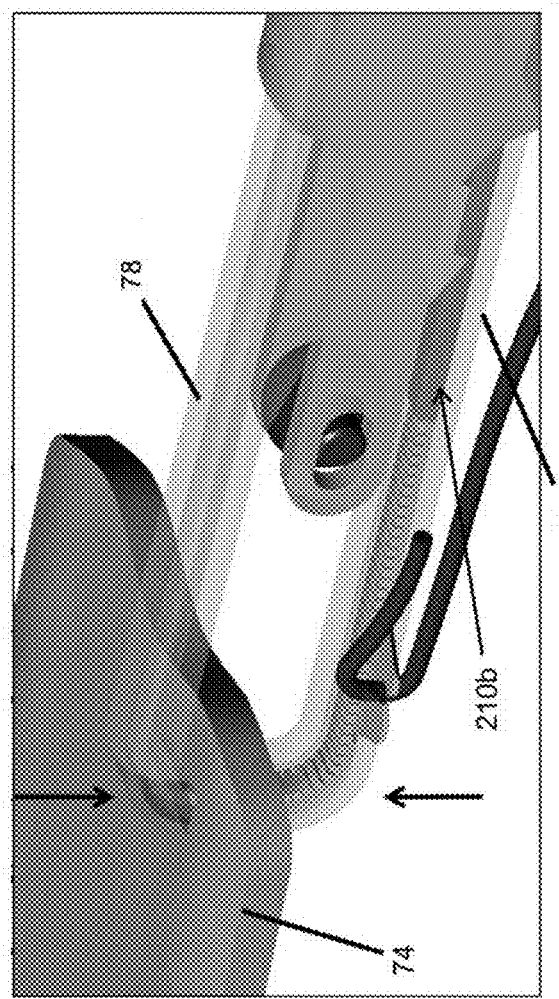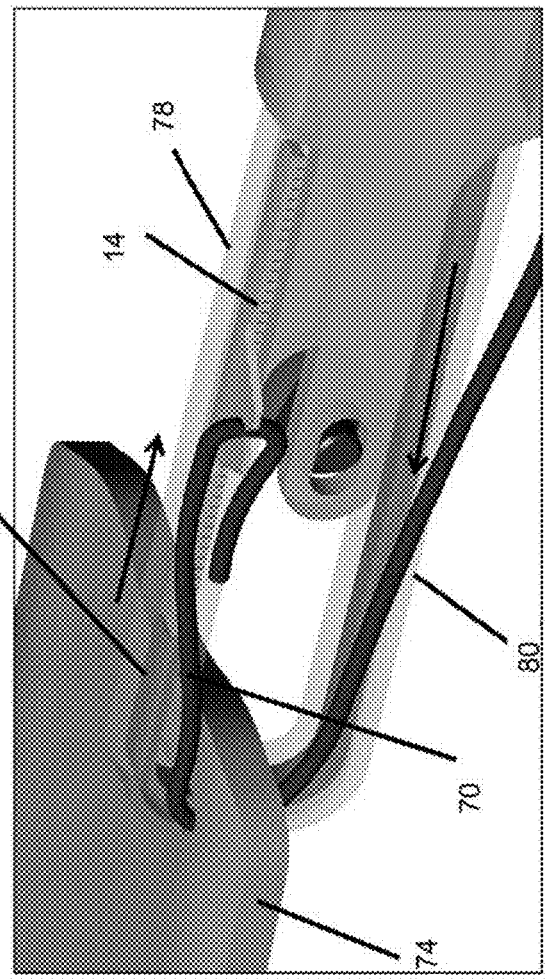

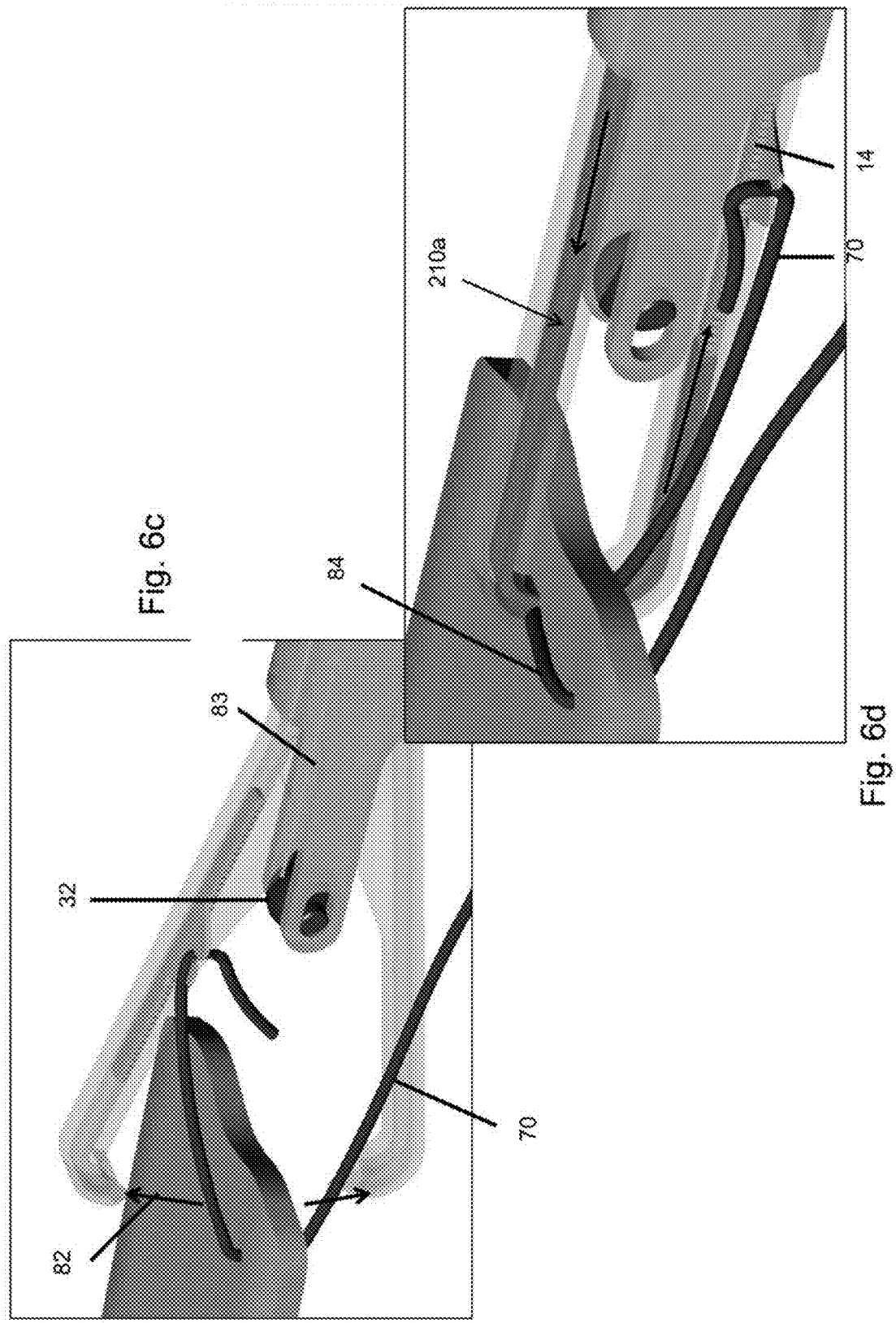

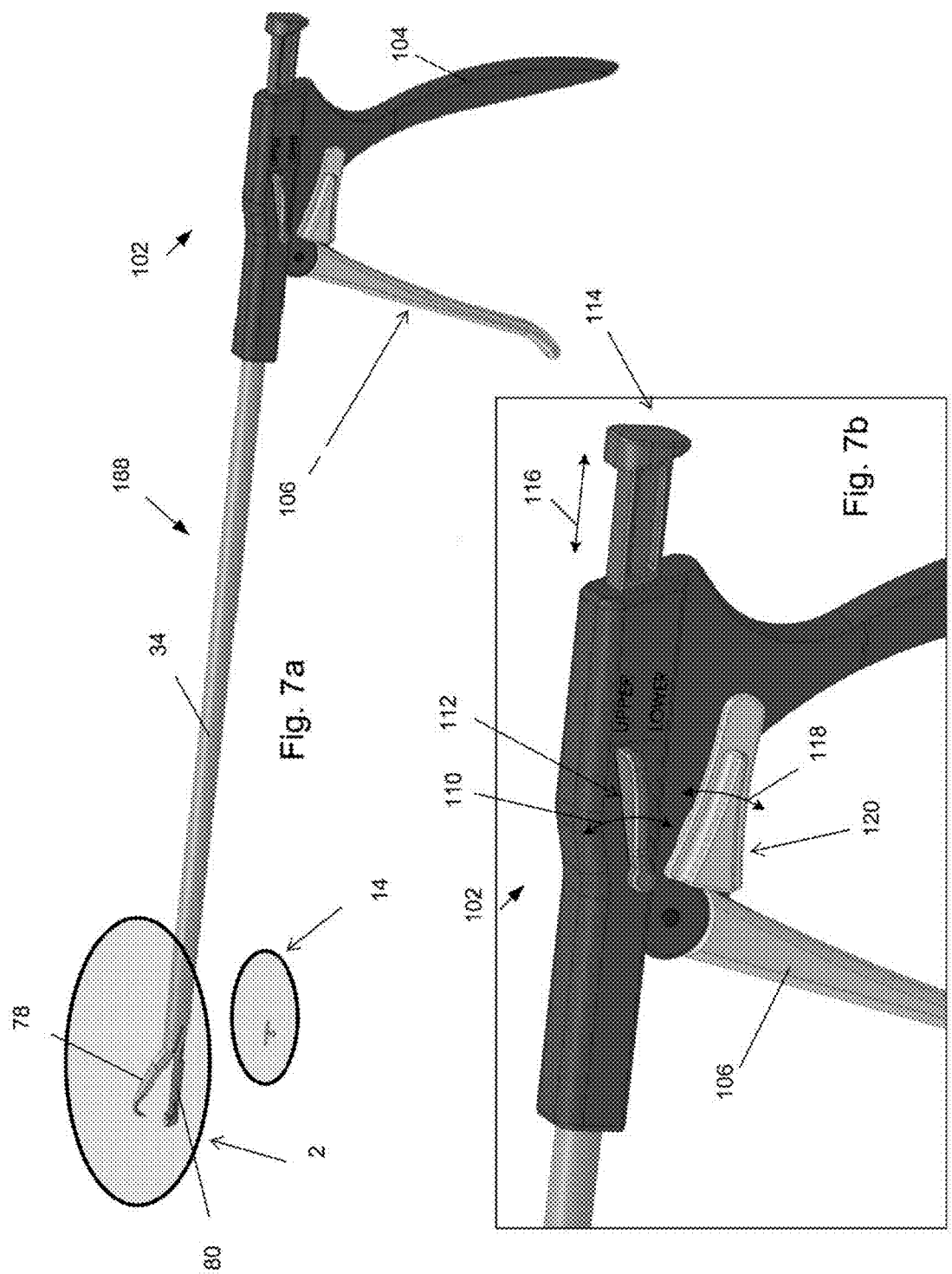

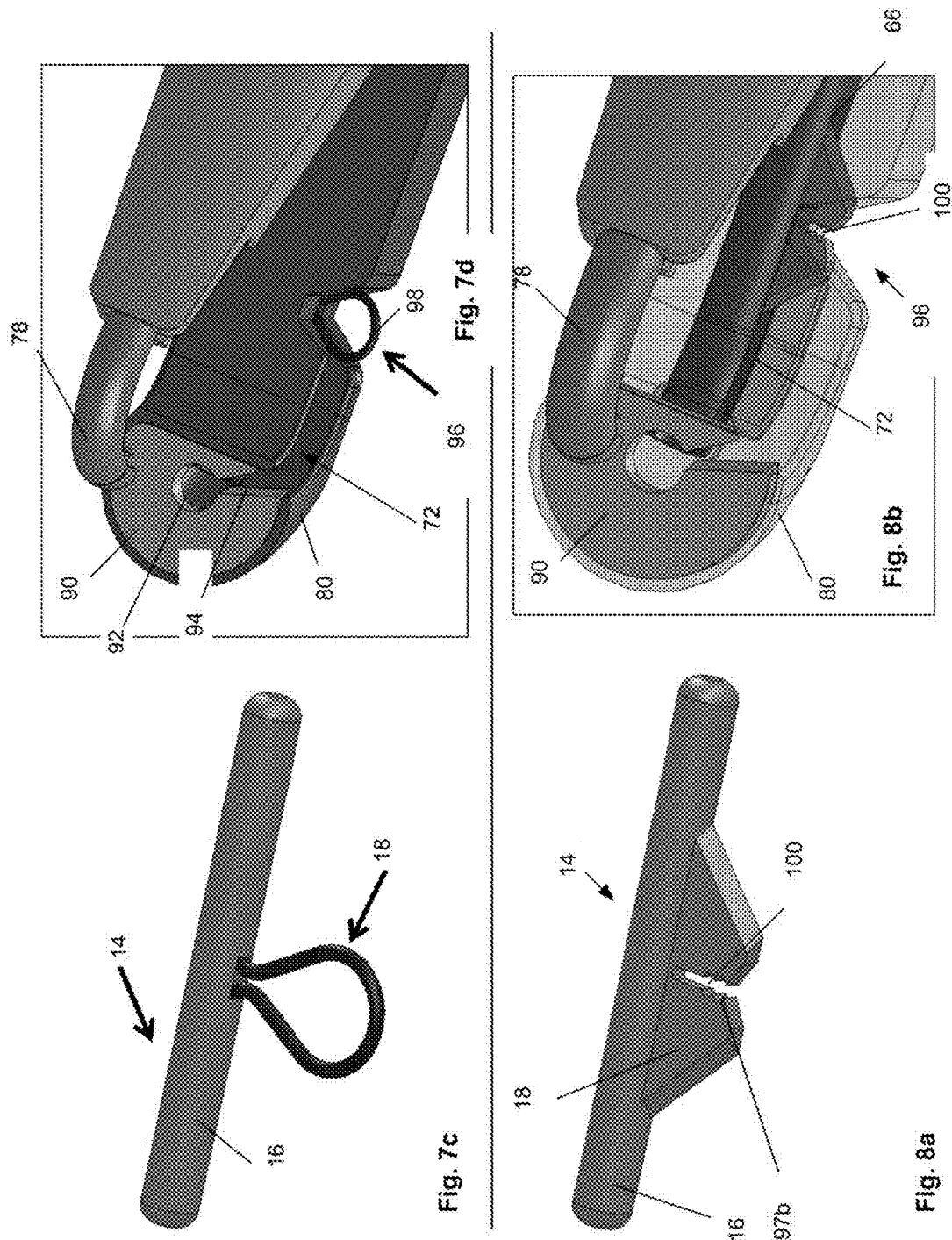

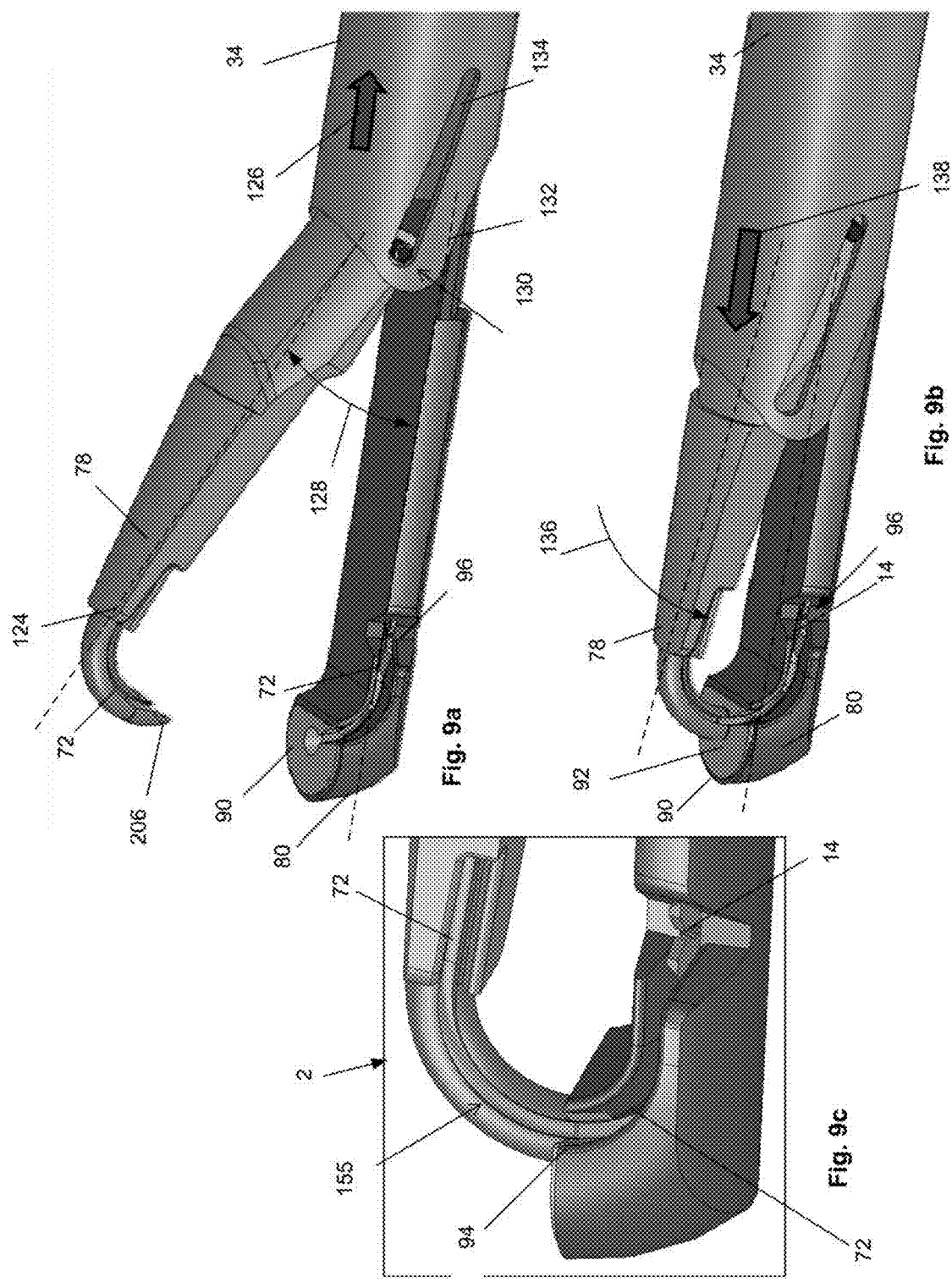

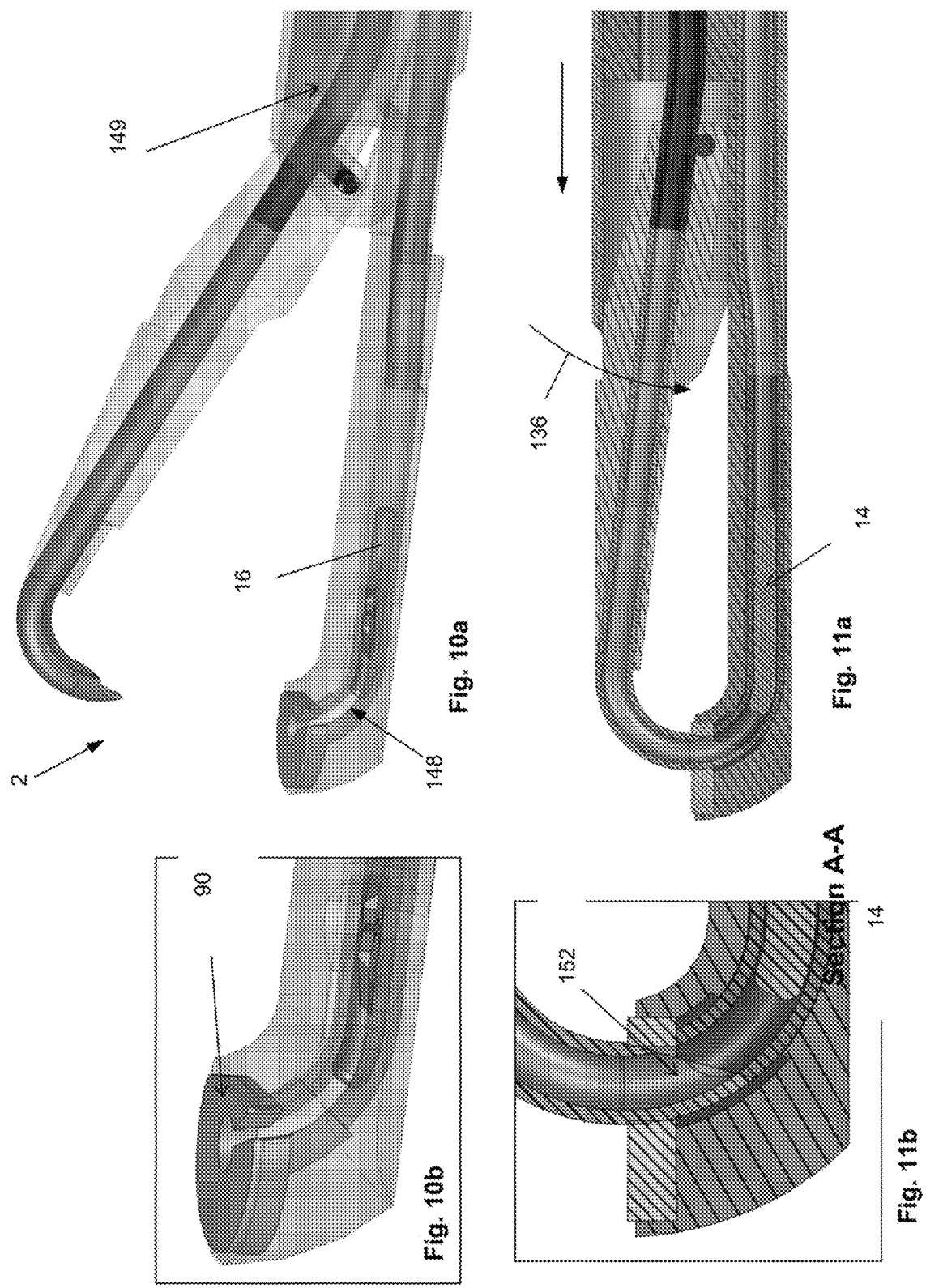

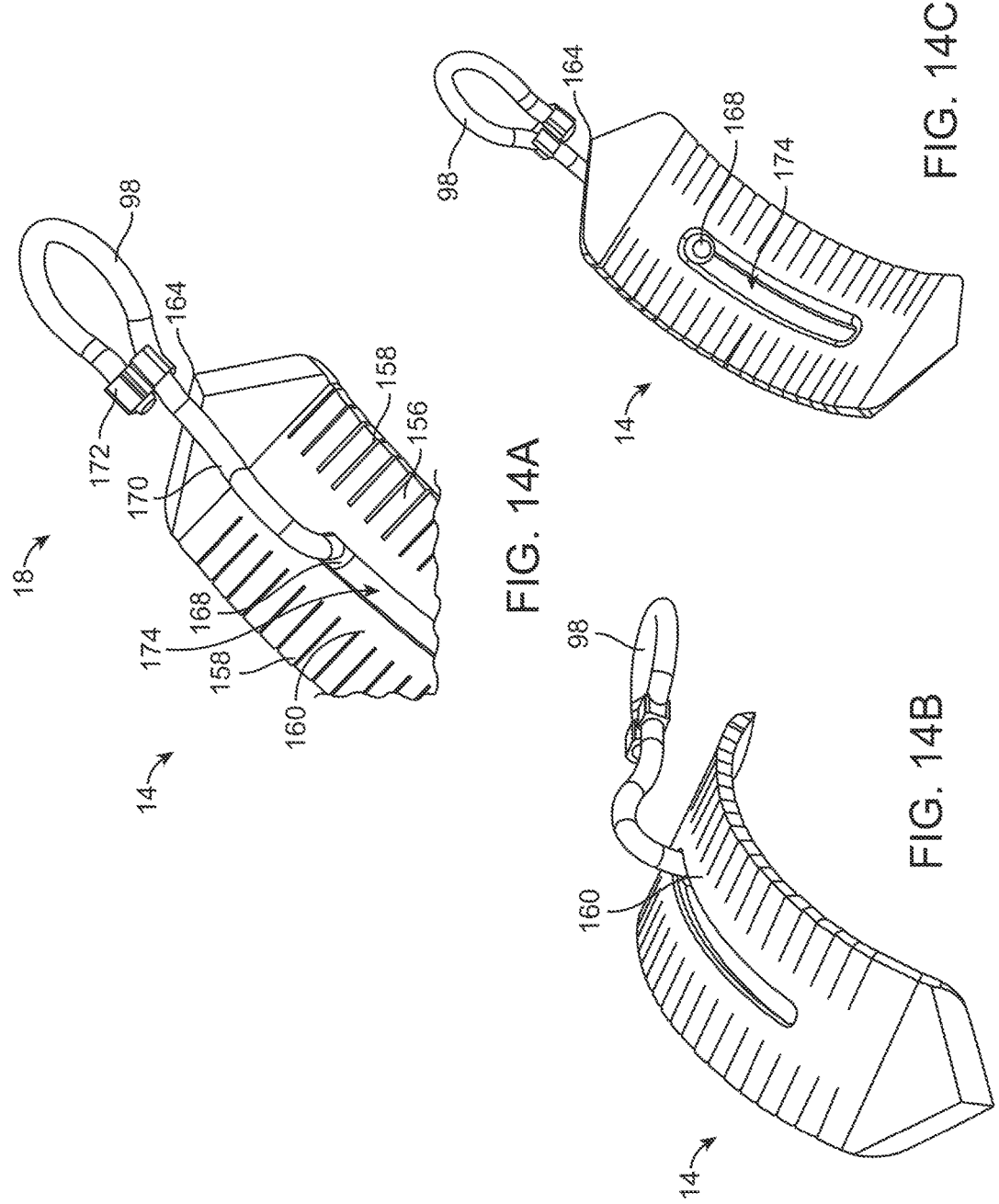

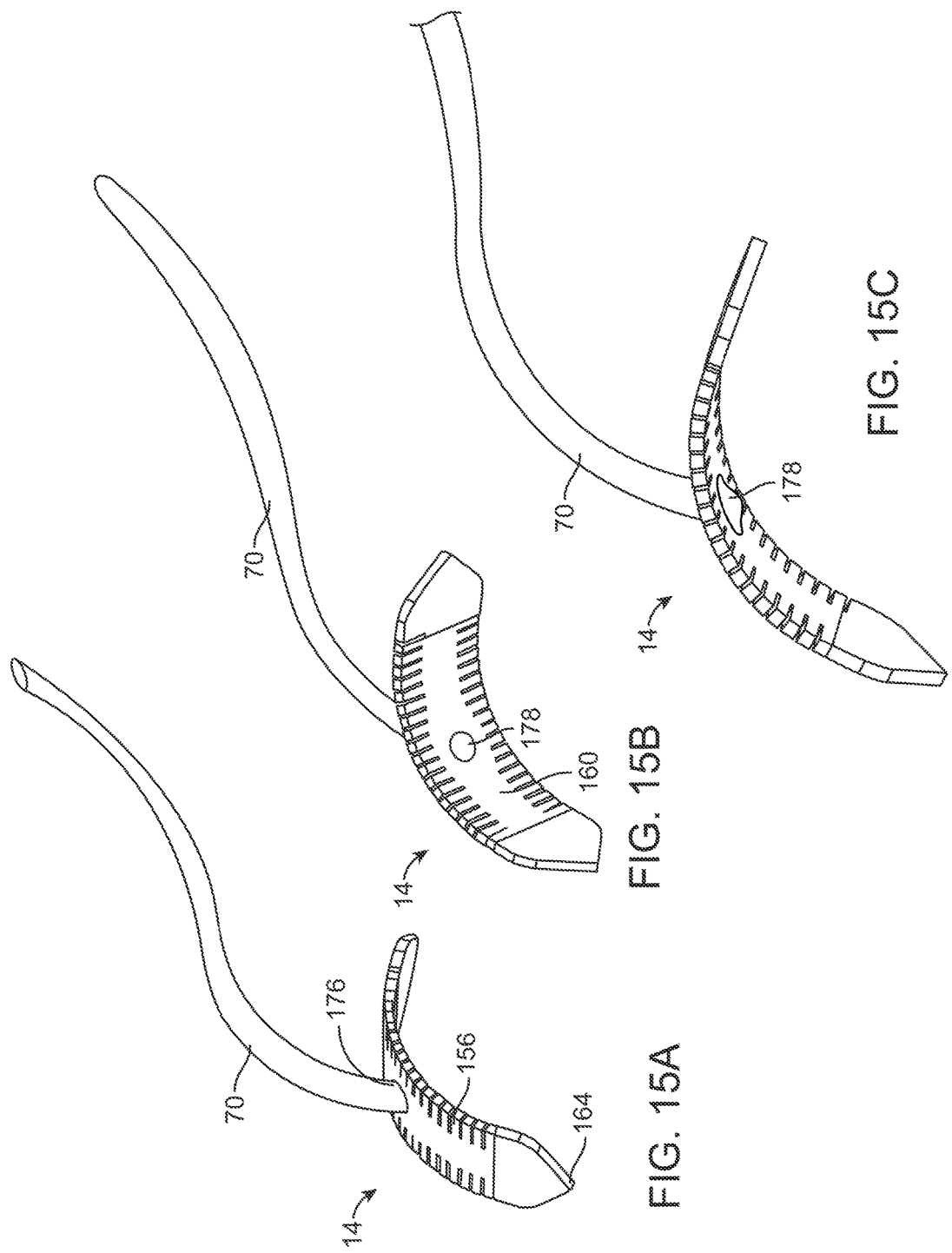

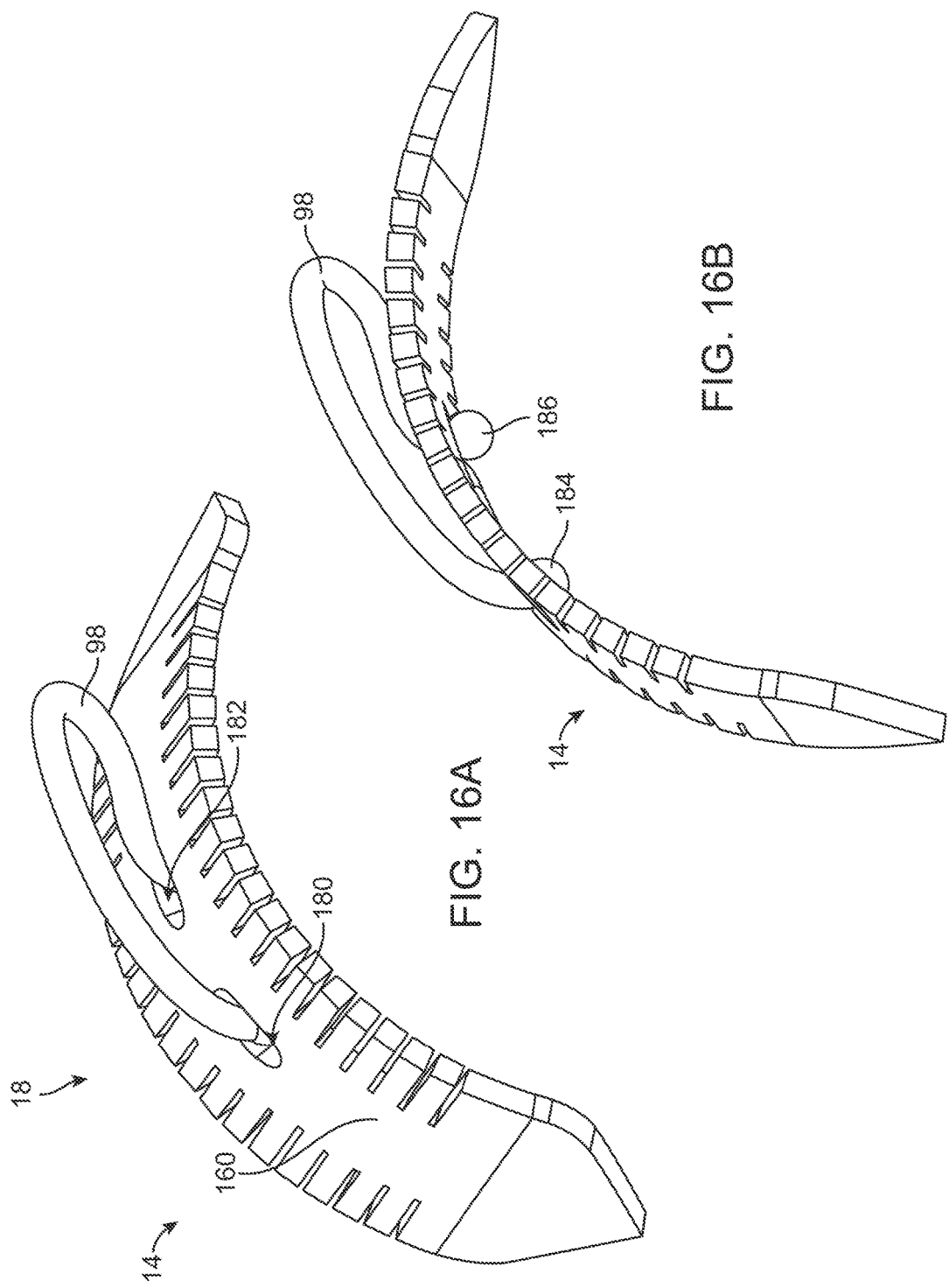

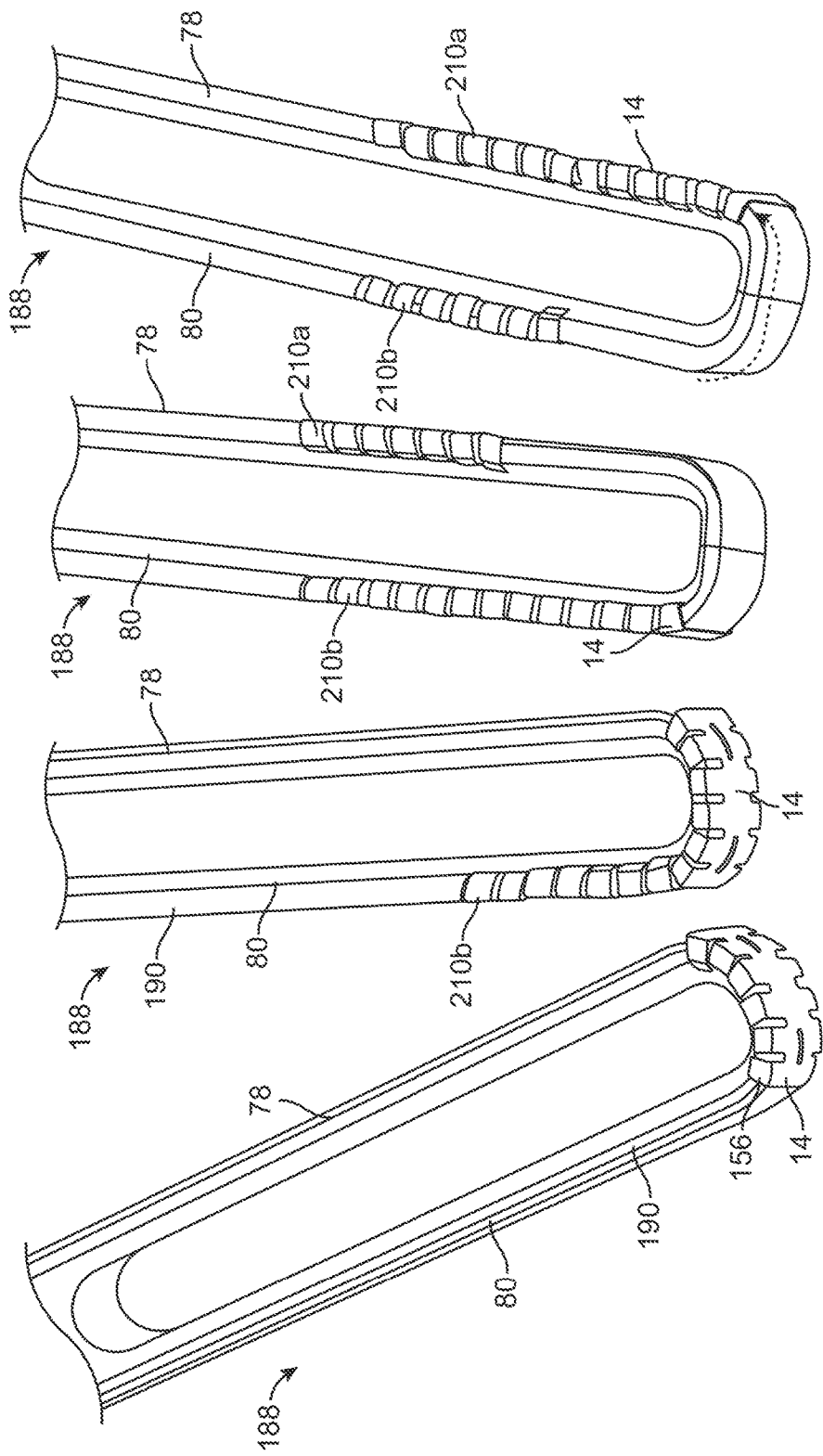

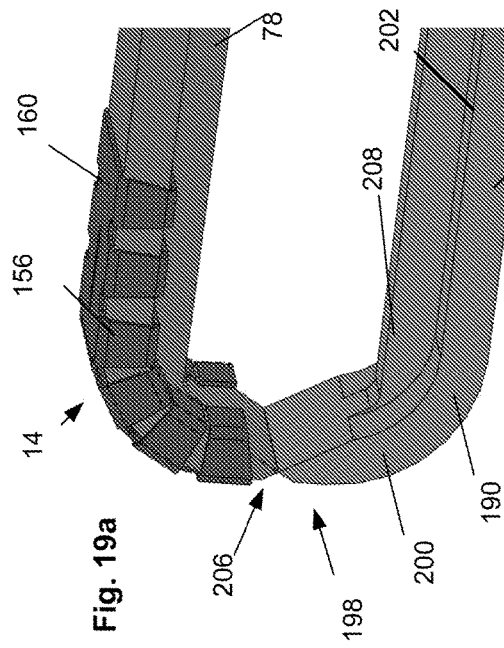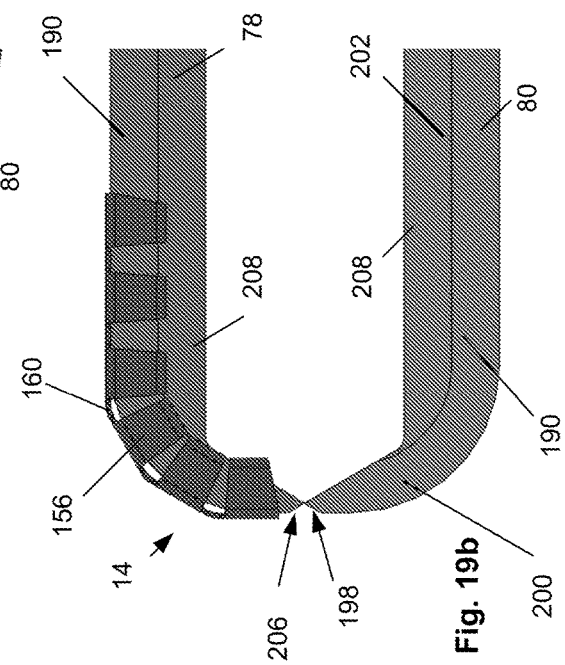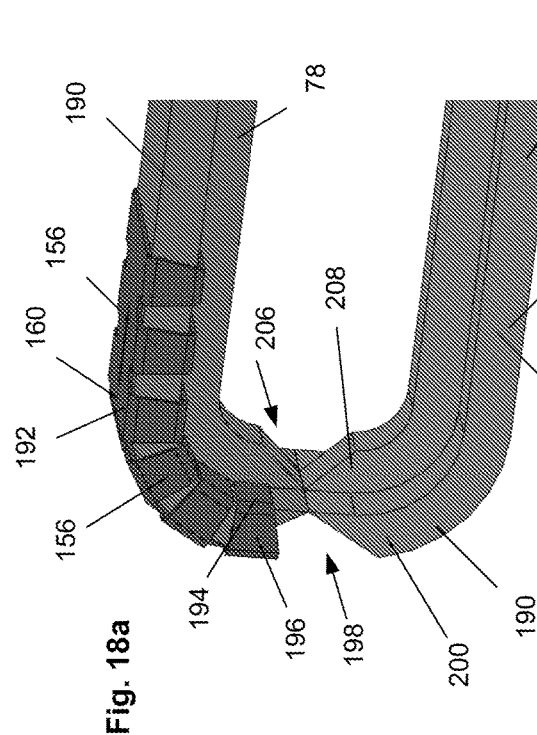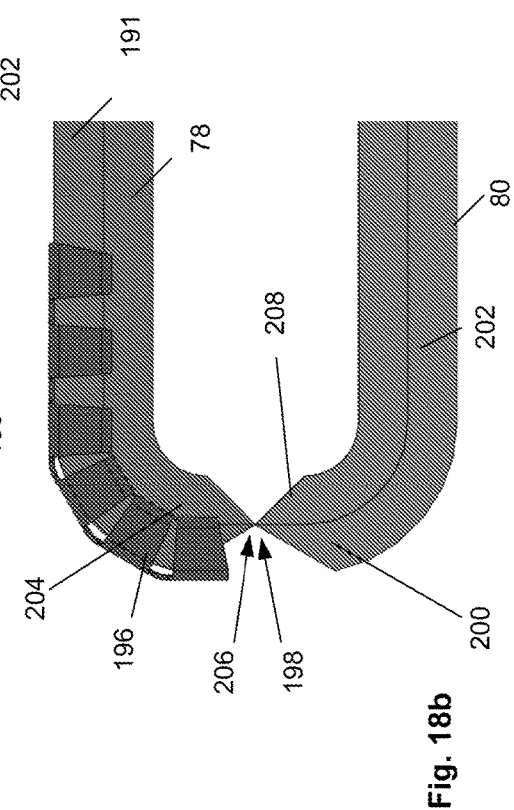

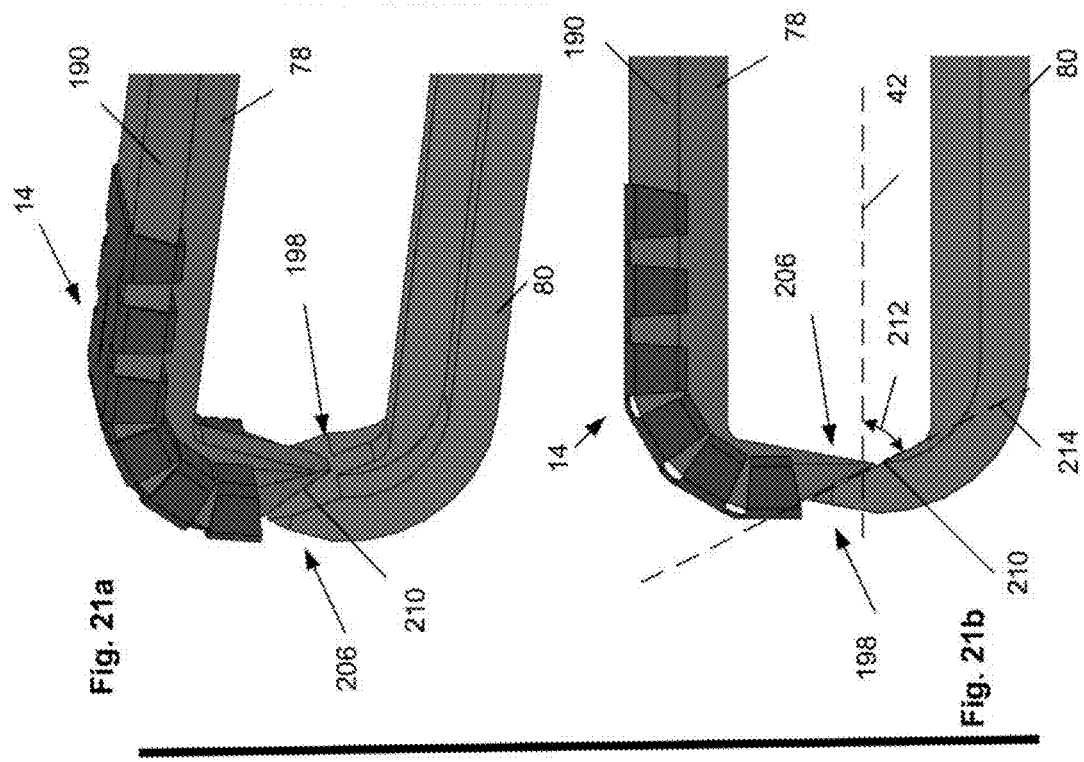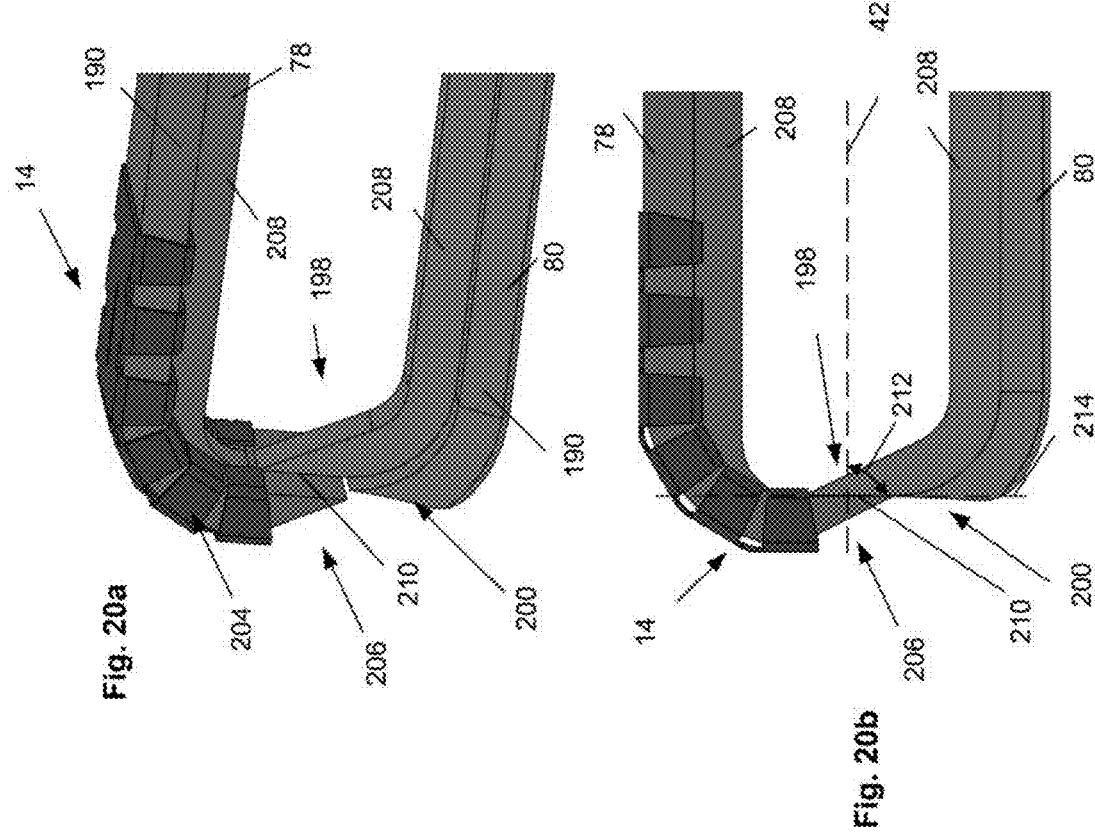

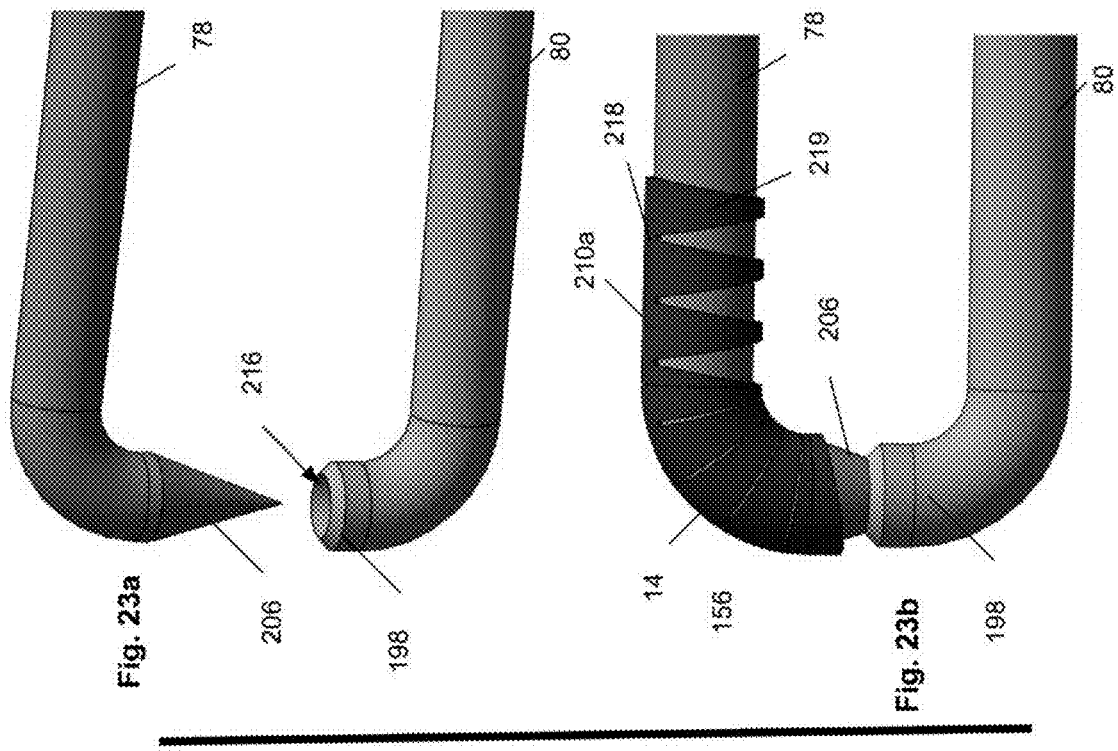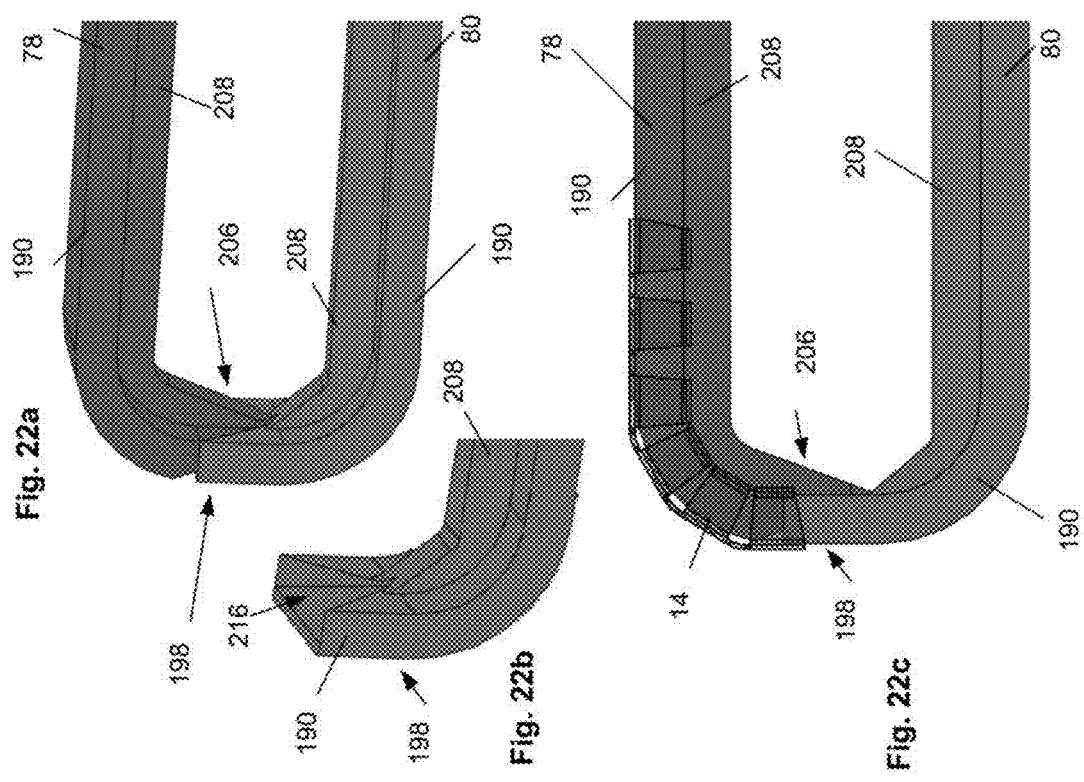

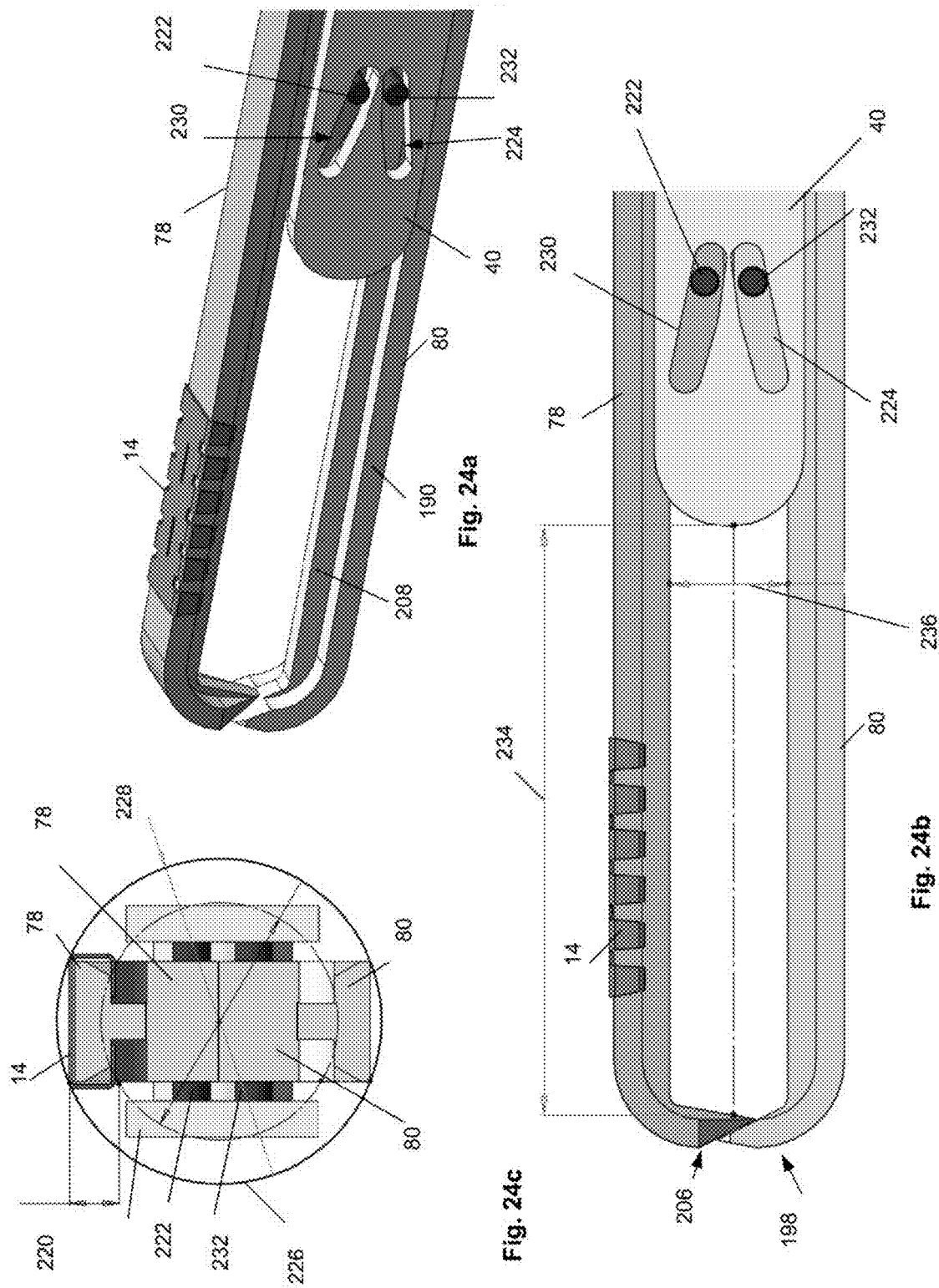

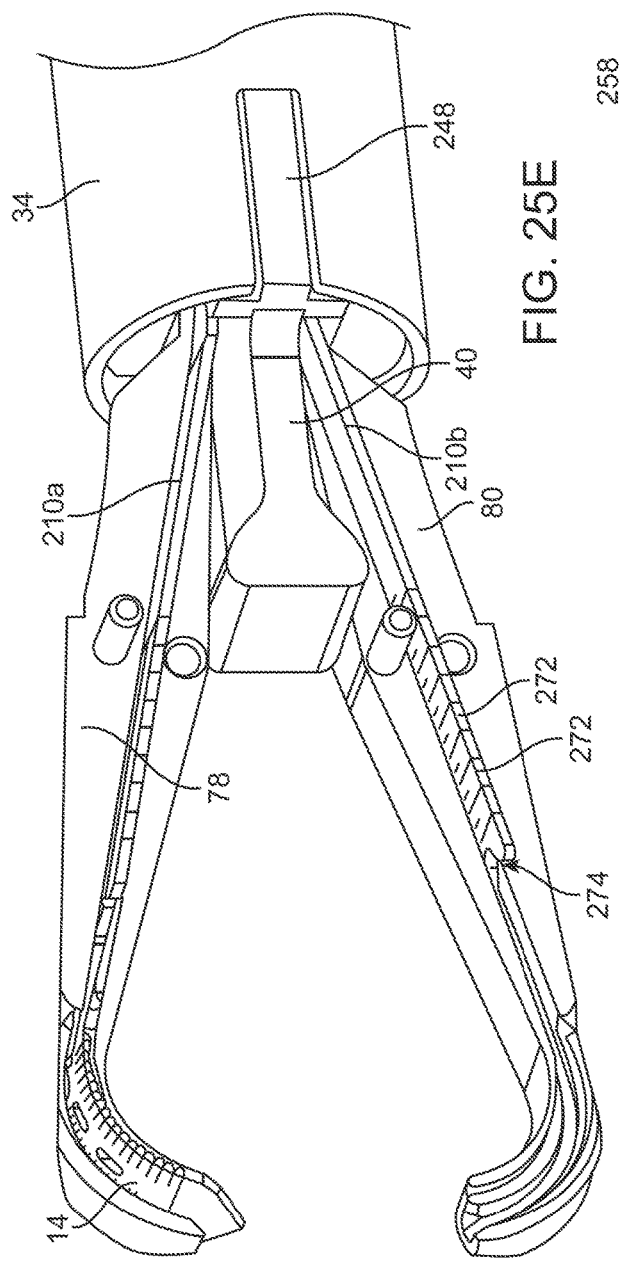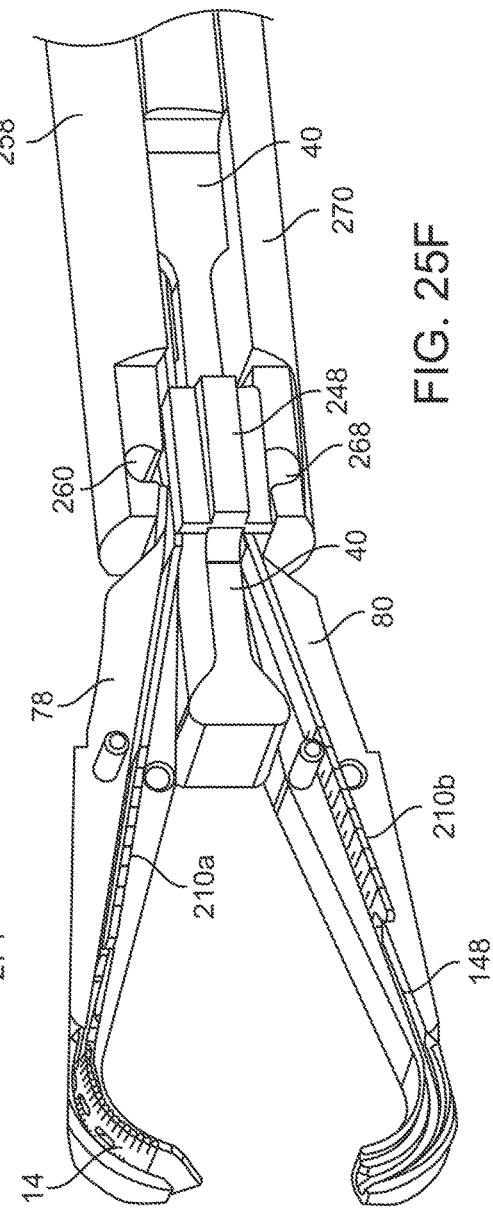

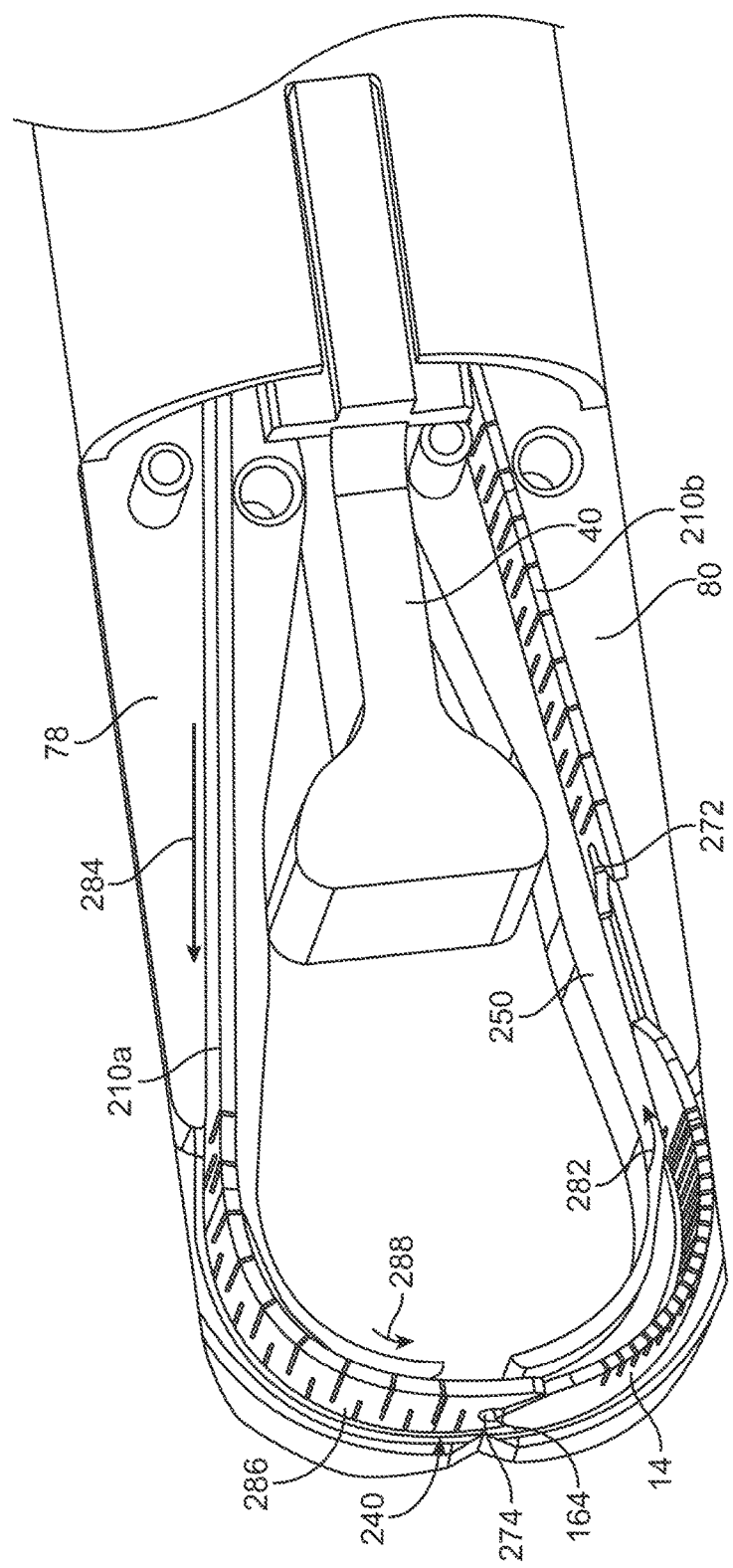

METHOD AND APPARATUS FOR PASSING SUTURE

CROSS-REFERENCE TO RELATED APPLICATIONS

This application claims the benefit of priority to U.S. Provisional Application No. 61/812,805 filed Apr. 17, 2013, the content of which is incorporated herein by reference in its entirety.

BACKGROUND

1. Field of the Invention

The present invention relates to system, methods, and apparatus for enhancing the advancement and retention of suture through tissue.

2. Description of Related Art

Suturing apparatus in the past have had an elongate shaft and a low profile distal clamping mechanism to facilitate their use through cannulas 226 in less invasive surgery. These devices have typically included opposing jaws which clamp onto the tissue to be sutured. The end segment of the suture is pre-positioned and secured at the distal end of one jaw member. Beyond the clamping motion, the mechanism for passing a suture between the jaws and through the tissue incorporates a bendable needle. The bendable needle advances distally within the jaw member, bringing it in contact with a segment of the suture.

The needle engages and secures the suture to carry it forward. This distal advancement of the bendable needle also results in the leading end of the needle to approach and engage a ramp 44 in the jaw member, deflecting the bendable needle in a direction toward the opposing jaw. The bending of the needle requires a high force and results in excess strain on the needle component. Fracture and failure of the bendable needle is a concern.

Additionally, the bendable needle is further advanced after being deflected in a direction extending away from the jaws, and potentially into unintended anatomy. Extension of the needle in this manner is a safety concern. Even after the apparatus has completed passing the suture through the tissue, the end segment of the suture must be retrieved by retracting the entire apparatus out of the cannula.

It would be advantageous to have an apparatus that could load and unload suture without the need to remove the apparatus from the surgical site.

It would be advantageous to have an apparatus that could pass (not load and unload) suture repeatedly through tissue without the need to remove the apparatus from the surgical site. It would also be advantageous for the suture shuttling mechanism (either needle or shuttle) to be entirely contained within the apparatus during operation to improve accuracy of suture placement and improve safety of needle or shuttle position during operation.

SUMMARY OF THE INVENTION

A device and method for passing suture through soft tissue is disclosed. The suture passer can perform multiple passes of the suture without withdrawing the suture passer from the target site, such as during a rotator cuff repair procedure.

The suture passing device can be made to have no mechanical pivoting links. The suture passing device can have no hinges in the jaw structure. The jaw structure can open and close with hinge-less action.

The suture can be mounted on the lateral side of the jaw structure.

A shuttle for holding and moving the suture can be captured and held within the jaws, for example creating a design of the device that has no loose parts capable of being separated from the device during use.

The jaws and/or the shaft or compression cover of the device can be made from a resilient metal such as Nitinol or any other material disclosed herein.

The device can pass suture repeatedly through tissue without the need to remove the apparatus from the surgical site or to load and unload the suture from the device. The suture shuttling mechanism (e.g., the needle and/or the shuttle) can be partially or entirely contained within the apparatus during operation to improve accuracy of suture placement and improve safety of needle or shuttle position during operation.

BRIEF DESCRIPTION OF THE FIGURES

FIGS. 1a, 1b and 1c are perspective, top and side views, respectively, of a variation of the suture passing device.

FIGS. 2a and 2b are a distant and close-up view, respectively, of a variation of the shuttle in a straight configuration.

FIG. 2c is a close-up view of the variation of the shuttle from FIGS. 2a and 2b in a curved configuration.

FIG. 3a is a close-up, perspective, partial see-through view of the distal end of a variation of the suture passing device attached to a length of a suture.

FIG. 3b is a close-up view of a portion of FIG. 3a.

FIGS. 4a and 4b are close-up perspective and side views, respectively, of the distal end of a variation of the suture passing device in a closed configuration.

FIG. 4c is a close-up of the distal end of FIGS. 4a and 4b.

FIG. 4d is a close-up perspective view of the distal end of the device of FIG. 4a in a closed configuration.

FIG. 5 is a variation of cross-section A-A of FIG. 1a with the device attached to a length of a suture.

FIGS. 6a through 6d illustrate a variation of a method of using a variation of the suture passing device to create a stitch in a piece of tissue.

FIGS. 7a and 7b are a side perspective view and a close-up a variation of the device with an exploded view of a shuttle, and a close-up of the proximal end of the device, respectively.

FIG. 7c is a close-up view of the variation of the shuttle in FIG. 7a.

FIG. 7d is a close-up view of the distal end of the variation of the device shown in FIG. 7a.

FIG. 8a illustrates a variation of the shuttle.

FIG. 8b illustrates a close-up view of a variation of the distal end of the device.

FIGS. 9a and 10a are side perspective and partial see-through side perspective views, respectively, of a variety of the device in an opened configuration.

FIGS. 9b and 11a are side perspective and side cross-section views, respectively, of a variety of a method for closing the jaws of the device of FIG. 9a.

FIGS. 9c and 11b are a close-up view and a side see-through view, respectively, of the distal end of the device in FIG. 9b.

FIG. 10b is a close-up partial see-through view of the distal end of the lower jaw of FIG. 10a.

FIGS. 14a through 14c are top end, front perspective, and bottom perspective views, respectively, of a variation of the shuttle.

FIGS. 15a through 15c are side perspective, bottom perspective, and side-bottom perspective views of a variation of the shuttle.

FIGS. 16a and 16b are top perspective and side perspective views of a variation of the shuttle.

FIG. 17a illustrates a variation of the device with the shuttle of FIGS. 12a through 12c.

FIG. 17b illustrates a variation of the device of FIG. 17a with a pusher.

FIGS. 17c and 17d illustrate a variation of the device of FIG. 17a with two pushers in different configurations.

FIGS. 18a and 18b are side perspective and side views, respectively, of a variation of the distal end of the device.

FIGS. 19a and 19b are side perspective and side views, respectively, of a variation of the distal end of the device.

FIGS. 20a and 20b are side perspective and side views, respectively, of a variation of the distal end of the device.

FIGS. 21a and 21b are side perspective and side views, respectively, of a variation of the distal end of the device.

FIGS. 22a and 22b illustrate a variation of the distal end and distal lower jaw, respectively, of the device.

FIG. 22c is a side view of the device of FIG. 22a with a shuttle.

FIGS. 23a and 23b are a variation of the distal end of the device in open and closed configurations, respectively with the device of FIG. 23b having a shuttle.

FIGS. 24a through 24c are side perspective, side and distal end views, respectively, of a variation of the device.

FIGS. 25a through 25f are bottom and side perspective, partial see-through (the upper jaw is see-through), longitudinal cross-section, partial cut-away close-up, and partial cut-away views, respectively, of the distal end of a variation of the device with the jaws in an opened configuration with the shuttle and pushers in various positions, and with the compression cover not shown in FIG. 25f for illustrative purposes.

FIG. 26 b does not show the pushers for illustrative purposes.

FIG. 27 is a close-up, partial cut-away view of the distal end of a variation of the device with the shuttle in the lower jaw and the upper pusher extending out of the upper jaw and partially entering the lower jaw.

DETAILED DESCRIPTION

Figure 12C:
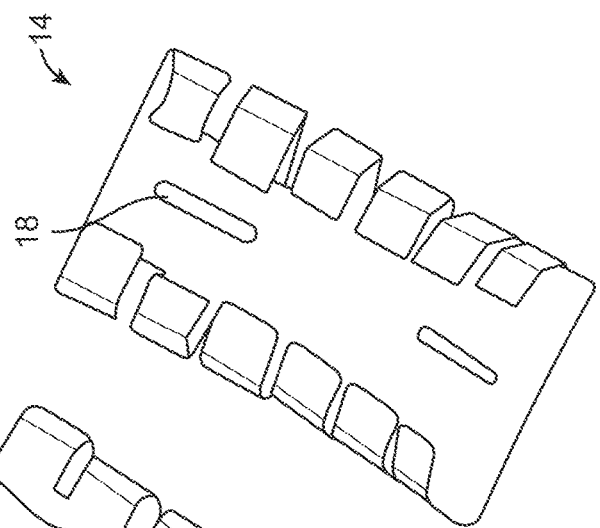
FIGS. 12a through 12c are side, top and bottom views, respectively, of a variation of the shuttle.

FIGS. 1a through 1c illustrate a suture passing device 188 that can be used to pass suture 70 through soft or hard tissue 74 without removing the device 188 or the suture 70 from the target site while creating one or more complete stitches.

The suture passing device 188 can have an ergonomic handle 104, a sliding tube actuator 6, and a distal end 2. The ergonomic handle 104 can be used to control the distal end 2. The ergonomic handle 104 can have a side knob 10. The ergonomic handle 104 can have a top knob 12. The top knob 12 and/or the side knob 10 can individually or in concert, advance and/or retract the upper 86 and/or lower pusher 76.

The sliding tube actuator 6 can have an outer compression cover 34 and an inner rod (not shown due to obstruction by the outer compression cover 34). The inner rod can be fixedly attached to the handle 104 and the proximal end of the jaw structure 28. The outer compression cover 34 can be radially outside of the inner rod. The outer compression cover can be actuated by the handle 104, for example be distally and proximally translated with respect to the handle 104 when the trigger 8 is squeezed or released.

FIGS. 2a and 2b illustrate that the device 188 can have a sliding ribbon shuttle 14 or needle held within the device 188. The shuttle 14 can have an elongated shuttle rail 16. The shuttle rail 16 can have numerous slits 20 along one or both sides of the shuttle rail 16. The slits 20 can be positioned at regular or irregular length intervals along the rail 16.

The shuttle 14 can have a suture holder 18 extending laterally from the rail 16. The shuttle 14, for example the suture holder 18, can extend out of the lateral side slot 72 of the arm structure. The suture holder 18 can extend from the left and/or right side of the device 188. The distal end 2 of the device 188 can be reversible so the suture holder 18 can be switched from one side of the device 188 to the other side of the device 188. The suture holder 18 can have a generally flat, isosceles trapezoid configuration. The suture holder 18 can have a suture holding notch 100. The notch 100 can have an inner hole 17a, an outer hole 17b contiguous with the inner hole 17a, and a first cleat 97a positioned between the inner hole 17a and the outer hole 17b. The notch 100 can have a second cleat 97b on the side of the outer hole away from the inner hole. The notch 100 can be configured to secure to suture 70. For example, the suture 70 can be compressed and friction fit in the inner cleat 97a.

The suture holder 18 can have a front leading edge and a rear leading edge. The edges can be slanted at a right or non-right angle with respect to the longitudinal axis of the rail 16. One or both of the edges can be sharpened to be traumatic to tissue 74, for example to cut through soft tissue 74. The edges can cut through tissue 74, allowing the suture holder 18 to pull the suture 70 through the tissue 74 immediately behind the respective edge.

The shuttle 14 can be made from a flexible polymer, such as PEEK, a resilient metal such as Nitinol, any material disclosed herein or combinations thereof. The shuttle 14 can be made from a molded polymer. The shuttle 14 can be pre-curved, for example to reduce resistance when going around curves in the tracks.

FIG. 2c illustrates that the rail 16 can curve at the locations of the slits 20, and/or the rail 16 can be pre-curved.

FIGS. 3a and 3b illustrate that the suture passing device 188 can capture or releasably attach to the suture 70 in the inner and/or outer cleats 97a and/or 97b of the suture holder 18. The suture 70 can be loaded or held laterally of the jaw structure 28, out of plane with the rotation of the jaws. The device 188 can make multiple passes of the suture 70 through the tissue 74 without extracting or reloading the suture passing device 188. The jaw structure 28 can resiliently deform open at the proximal end of the jaw structure 28, having no hinge. The jaws can be opened and/or closed with no mechanical pivots or linkages in the jaw structure 28.

FIG. 4a illustrates that the suture passer device 188 can have a jaw structure 28 with a top jaw 30 and a bottom jaw 38. The entire jaw structure 28 can be an integral piece of material, such as a single molded, cast, or cut element of Nitinol, other resilient metal or polymer, any other material listed herein, or combinations thereof. The jaw structure 28 can be configured to be in an opened configuration (as shown in FIG. 4d) when in an unbiased configuration (i.e., when no external forces are applied).

The jaw structure 28 can have a jaw structure longitudinal axis 42. Each jaw can also have a respective jaw longitudinal axis along the jaw.

The inside channel of the compression cover 34 can be sized and shaped to fit over the jaw structure 28 with minimum clearance when the jaw structure 28 is in a closed configuration. When the compression cover is translated distally 138 with respect to the jaw structure 28, as shown by arrow, the compression cover 34 can press the top and bottom jaws 38 toward the jaw structure longitudinal axis 42. The jaw structure 28 can be fully compressed into a closed configuration, as shown in FIGS. 4a through 4c. In this way, when an actuation lever such as the trigger 8 is actuated, the channel or compression cover 34 can advance to cam closed the jaws. The jaws can pre-pierce the tissue and establish a continuous track for the shuttle to pass through the tissue.

The compression cover 34 can be attached to an opening ball 32 positioned between the first and second jaws.

FIG. 4b illustrates that the opening ball 32 can be rotatably or fixedly attached to a ball axle 52 passing laterally through the opening ball 32. The ball axle 52 can extend out from the lateral sides of the ball 32. The ball axle 52 can be slidably received by axle slots 50 formed through distal arms 54 or extensions 138 of the compression cover 34. When the jaw structure 28 is in a closed configuration, the ball axle 52 can abut and interference fit against the proximal end of the axle slot 50, for example to prevent overextension of the compression cover 34 over the jaw structure 28. When the jaw structure 28 is in an opened configuration, the ball axle 52 can abut and interference fit against the distal end 2 of the axle slot 50, for example to prevent overrotation of the jaws and/or pulling the ball 32 past the ramps 44 on the inside of the jaw structure 28.

FIG. 4c illustrates that the bottom track 66 can distally terminate in a bottom track port 62. The top track 64 can distally terminate at a top track port 60. The top track port 60 can align with and be adjacent to (as shown) or in contact with the bottom track port 62 when the jaw structure 28 is in a closed configuration with the first jaw tip 46 interdigitating with the second jaw tip 48. The tracks of the upper jaw 78 and bottom jaw 38 can form a continuous path when the jaw structure 28 is in a closed configuration. The first jaw tip 46 can interdigitate with and be adjacent or in contact with the second jaw tip 48 when the jaw structure 28 is in a closed configuration.

FIG. 4d illustrates that that compression cover 34 can be translated proximally 126, as shown by arrow, with respect to the jaw structure 28. The ball axle 52 can slide to the distal end 2 of the axle slot 50. The axle slot 50 can then pull the ball axle 52, and therefore the opening ball 32, proximally. The opening ball 32 can then press against the inside surface ramp 44 of the first jaw and/or second jaw. The first jaw tip 46 and/or second jaw tip 48 can then rotate away from the opposing jaw tip. The jaw structure 28 can then be in an opened configuration, as shown.

The proximal ends of the jaws can be rigid or flexible, for example to bend around the opening of the compression cover 34 when the jaws are in an opened configuration. The entire jaws or just the proximal ends of the jaws can be made from Nitinol, for example with the distal ends of the jaws made from stainless steel.

FIG. 5 illustrates that the side slot 72 can extend laterally from one side of the tracks. The rail 16 of the shuttle 14 can be taller than the height of the side slot 72. The rail 16 can be too large to pass through the side slot 72. The suture holder 18 can extend laterally from the rail 16 through the side slot 72. The suture holder 18 can hold the suture 70 laterally spaced away from the jaw.

FIG. 6a illustrates that the upper jaw 78 and the lower jaw 80 can be closed, as shown by arrows, and compressed through tissue 74, such as soft tissue 74 in the rotator cuff or other joint. The upper jaw tip 206 and/or the lower jaw tip 198 can pierce the tissue 74. The upper jaw tip 206 and the lower jaw tip 198 can interdigitate in or adjacent to the tissue 74. The hole created by the touching or interdigitating of the upper jaw tip 206 and/or the lower jaw tip 198 can be a hole in the tissue 74 through which the shuttle 14 and/or suture 70 can pass. The compression cover can be pushed distally 138 to further compress the first jaw toward the second jaw, for example to force the jaw tips to pierce the tissue 74.

The lower pusher 76 can be advanced distally, as shown by arrow, as controlled by the handle 104. The lower pusher 76 can force or push the shuttle 14 through the track to move distally and to carry the suture 70 with the shuttle 14.

FIG. 6b illustrates that the lower pusher 76 can continue to be pushed by the handle 104. The lower pusher 76 can push the shuttle 14 through the tissue 74. The front edge 22 of the suture holder 18 can cut through the tissue 74 and the suture holder 18 can pull the suture through the cut created in the tissue 74 by the front edge 22 and/or through the piercing created in the tissue 74 by the tips of the jaw. The pusher and the shuttle 14 can move along the longitudinal axis of the jaws.

The shuttle 14 can then be positioned entirely in the track of the upper jaw 78. The lower pusher 76 can then be withdrawn from the track of the upper and/or lower jaw 80, and/or the lower pusher 76 can be left in place but the resistive force can be removed, allowing the lower pusher 76 to slide freely in the tracks.

FIG. 6c illustrates that the compression cover can then be translated proximally 126 (e.g., by releasing or squeezing the trigger 8), as shown by arrow 83. The ball axle 52 can be pulled proximally, forcing the opening ball 32 against the inner surface of the top and/or bottom jaws 38. The opening ball 32 can thus resiliently force open the top and/or bottom jaw 38. The jaws can then be unclamped (i.e., rotated open, as shown by arrows 82), and be cleared from the tissue 74.

The device 188 can then be shifted to a position where the distal end 2 of the device 188 is adjacent (e.g., lateral) to where the suture initially passed through the tissue 74.

FIG. 6d illustrates that the jaw can then be closed, piercing the tissue 74 adjacent to the first passage of the suture 70 through the tissue 74. The upper pusher 86 can then be forced distally, as shown by arrow, by the handle 104. The upper pusher 86 can force or push the shuttle 14 along the track in the reverse direction from shown in FIGS. 6a and 6b. The rear edge 24 of the suture holder 18 can then cut the tissue 74 as the suture holder 18 passes through the tissue 74, carrying the suture 70 through the tissue 74. Thus a mattress stitch of the suture 70 through the tissue 74 can be created.

The shuttle 14 can then be in the home position, as shown in FIG. 6a. The upper pusher 86 can then be withdrawn from the track of the upper and/or lower jaw 80, and/or the upper pusher 86 can be left in place but the resistive force can be removed, allowing the upper pusher 86 to slide freely in the tracks. The jaws can be reopened and repositioned, and the device 188 can create another stitch repeating the method shown in FIGS. 6a through 6d. The jaws can be reopened and removed from the target site when the stitching is complete or to deliver a second stitch.

FIG. 7a illustrate that the device 188 can have a base 102 and a handle 104 extending from the base 102. The device 188 can have a rotatable lever 106 rotatably attached to the base 102 or handle 104. The device 188 can have a compression cover 34 translatably attached to and extending distally from the base 102.

The distal end 2 of the device 188 can have the upper and lower jaws 80. The upper jaw 78 can be rotatable with respect to the lower jaw 80 and vice versa.

The compression cover 34 can be slidably attached to one or both jaws. The rotatable lever 106 can be attached to the compression cover 34. For example, squeezing and rotating the lever 106 toward the handle 104 can push the compression cover distally 138 with respect to the jaws. The compression cover can distally slide over the jaws, rotating the upper jaw 78 toward the lower jaw 80 and closing the jaws. The lever 106 can be spring loaded to rotate away from the handle 104, proximally retract the compression cover 126, and return the jaws to an open configuration when external pressure or squeezing is no longer applied to the lever 106.

FIG. 7b illustrates that a pusher shaft or button can extend distally from the base 102 or handle 104. The pusher shaft or button can be translated with respect to the base 102 and/or handle 104, as shown by arrows. The pusher shaft can be configured to push and/or pull one or both pushers. Pressing or pulling on the pusher shaft can translate the pusher. A single pusher shaft or button can be toggled between both pushers.

A pusher toggle, such as a side paddle 112 can extend from the lateral side of the base 102. The side paddle 112 can be positioned on the top or bottom of the base 102 or the handle 104. The side paddle 112 can rotate 110 with respect to the base 102, as shown by arrow. The side paddle 112 can be configured to orient the pusher shaft or button to translate the upper pusher 86 or lower pusher 76 depending on the position of the side paddle 112.

The device 188 can have a lever 106 lock 120. The lever 106 lock 120 can extend laterally from the base 102. The lock 120 can rotate 118, as shown by arrows, with respect to the base 102. The lock 120 can be configured to fix or secure the lever 106 closed or in a particular angular position with respect to the base 102. For example, the lever 106 lock can fix the lever 106 closed, in turn fixing the jaws in a closed configuration.

FIG. 7c illustrates that the shuttle 14 can have a rail 16 that can be a cylindrical tube or sleeve. The rail 16 can be made from Nylon, other materials disclosed herein, or combinations thereof. The rail 16 can have rounded (e.g., hemi-spherical) or flat terminal longitudinal ends.

The shuttle 14 can have a suture holder 18 that can be a wire loop 98 extending laterally from the rail 16. The wire loop 98 can have a wire. The wire loop 98 can extend in a flat plane. The terminal ends of the wire can be anchored—e.g., removably or fixedly attached to the rail 16, for example through a port or slot in the lateral side of the rail 16. The suture 70 can extend through and remain within the area defined by the perimeter of the wire loop 98 while the suture 70 is retained by the suture 70 passer.

FIG. 7d illustrates that the lower jaw 80 (as shown) and/or upper jaw 78 can have one or more loading notches or docks 96. The loading dock 96 can expose the suture holder 18, such as the wire loop 98, for suture 70 loading/unloading. The suture holder 18 can extend into the loading notch. For example the wire loop 98 can extend through the side slot 72 and into the holding notch 100 with the shuttle 14 is in a position for loading and/or unloading the suture 70 to and/or from the shuttle 14. For example, the shuttle 14 can be at the proximal-most position for the shuttle 14 on the bottom track 66 when the suture holder 18 is aligned with the loading dock 96. The side slot 72 can terminate at the loading dock 96, fir example, interference fitting the wall of the loading dock 96 against the shuttle 14 and/or suture holder 18 to prevent further translation of the shuttle 14 proximally along the jaw.

The lower 80 and/or upper jaws 78 can have a septum 90 can cover a medial terminal face at the distal end 2 of the lower jaw 80 (as shown) and/or upper jaw 78. The septum 90 can be a flexible material that can be configured to seal around all or part of the shuttle 14 as the shuttle 14 passes through the septum 90. For example, the septum 90 can be made from a fabric, or a solid panel of polymer such as polyurethane or polyester.

The septum 90 can have a septum rail port 92. The septum rail port 92 can be aligned with the terminal end of the bottom track 66 and/or top track 64.

The septum 90 can have a septum slot 94. The septum slot 94 can be aligned with the side slot 72 of the bottom track 66 and/or the upper track 264.

The septum 90 can be configured to wipe or squeegee debris, such as tissue 74 and biological fluids, from the shuttle 14 as the shuttle 14 passes through the septum 90, for example to prevent or minimize debris and fluids entering the top and/or bottom tracks 66.

FIG. 8a illustrates that the shuttle 14 can have a rail 16 that can have a cylinder and suture holder 18 can be as described in FIGS. 2b and 2c. The holding notch 100 can have angular cleats 97. The holding notch 100 can extend to side of the rail 16.

FIG. 8b illustrates that the shuttle 14 can be positioned so the holding notch 100 of the suture holder 18 can be in the loading dock 96 when the suture 70 is attached to or removed from the holding notch 100. The suture 70 can be pressed into (e.g., for attaching) or pulled from (e.g., for removing, detaching or repositioning) the holding notch 100. A longitudinally opposing pair of first cleats 97 can laterally friction fit or interference fit the suture 70 in the holding notch 100. A longitudinally opposing pair of second cleats 97 can medially friction fit or interference fit the suture 70 in the holding notch 100 (i.e., the suture 70 can be radially fixed between the pair of first cleats 97 on a lateral side of the suture 70 and the pair of second cleats 97 on a medial side of the suture 70).

The suture 70 can be radially fixed between a pair of longitudinally opposed cleats 97 that can dig into and compress or puncture the external surface of the suture 70.

The shuttle 14 can interference fit or otherwise be stopped by the lower jaw 80 from moving proximal to a position where the holding notch 100 is exposed in the loading dock 96.

FIGS. 9a, 10a and 10b illustrate that the device 188 can be in an open configuration with the upper jaw 78 positioned rotated away from the lower jaw 80. The upper jaw 78 can have an upper jaw longitudinal axis. The lower jaw 80 can have a lower jaw longitudinal axis 132. The lower jaw longitudinal axis 132 (as shown) or the upper jaw longitudinal axis 124 can be parallel and/or collinear with the compression cover longitudinal axis. The upper jaw longitudinal axis 124 and the lower jaw longitudinal axis 132 can intersect at a jaw angle 128. When the jaws are in an open configuration, the jaw angle 128 can be from about 30° to about 45°, more narrowly from about 30° to about 40°.

The compression cover 34 can be translated and retracted proximally, as shown by arrow 126, away from the jaws. The upper jaw 78 can have a slot slide pin 130 that can extend laterally from one or both lateral sides of the proximal end of the upper jaw 78.

The distal end 2 of the compression cover 34 can have one or more ramp slots 134 on one or both lateral sides of the compression cover 34. The ramp slot 134 can narrow as the ramp slot 134 extends proximally (i.e., widen as the ramp slot 134 extends distally). The ramp slot 134 can be at a non-zero angle (i.e., non-aligned) to the longitudinal axis of the compression cover 34.

The slot slide pin 130 can be configured to extend through the ramp slot 134. The slot slide pin 130 can slide within the ramp slot 134. The slot slide pin 130 can friction fit into the narrower, proximal end of the ramp slot 134, for example friction-fitting the jaws in a closed configuration and providing tactile feedback to the user of the jaw angle 128.

FIG. 10a illustrates that the upper track can pass through a hinge tube 149 where is extends past the distal opening of the compression cover 34 and into the upper jaw. The hinge tube 149 can be made from nitinol, for example. The hinge tube 149 can flex when the upper jaw is rotated. The hinge tube 149 can be an integrated length of the entire upper track, or can be a separate length of tube attached on one or each end to the remainder of the upper track.

FIGS. 9b and 11a illustrate that the compression cover 34 can be distally extended or advanced, as shown by arrow 138, with respect to the jaws. The compression cover 34 can force the jaws to rotate toward each other to a closed configuration. For example, the upper jaw 78 can rotate, as shown by arrow 136, while the lower jaw 80 remains in a rotationally fixed position with respect to the compression cover 34, or vice versa, or the jaws can both rotate with respect to the compression cover 34. Thus, a lever, such as the trigger 8, can be actuated to advance the outer tube or compression cover 34 to cam closed the jaws.

When the jaws are in a closed configuration, the jaw angle 128 can be from about 0° to about 3°, more narrowly from about 0° to about 2°, for example about 0°.

FIGS. 9c and 11b illustrate that the upper jaw tip 206 can be pressed into and through the septum rail port 92. The top or upper track 264 can form a continuous lumen 152 with the bottom or lower track 148, for example, that the shuttle 14 can slide through.

A side slot 72 of upper jaw 78 can align with a side slot 72 of lower jaw 80. The suture holder 18 can extend through the side slot 72 and hold the suture 70 in the side slot 72. The suture holder 18 can translate suture 70 back and forth between the upper 78 and lower jaws 80 in the side slot 72 as the shuttle 14 is translated back and forth between the upper 78 and lower jaws 80.

Figure 12B:
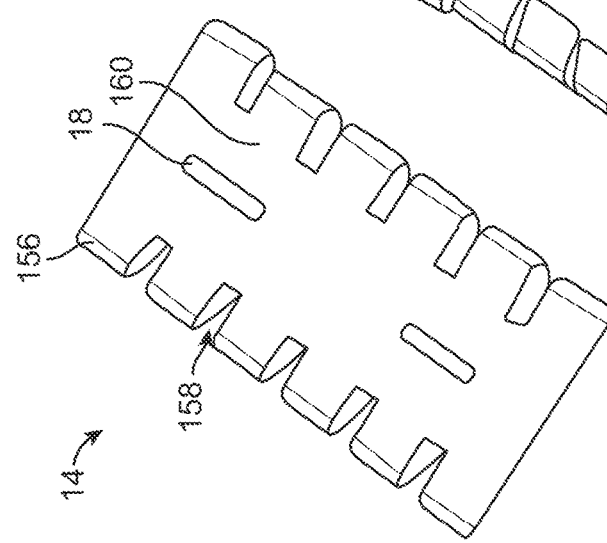
Figure 12A:
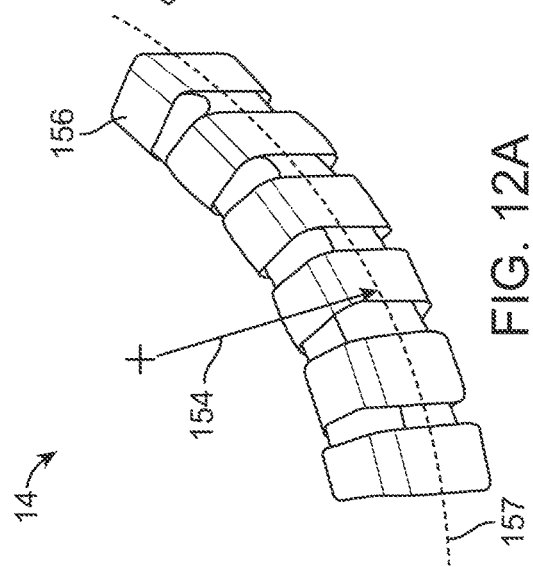

FIGS. 12a through 12c illustrate that the shuttle 14 can a rail 16, for example a shuttle spine 160, and shuttle 14 lateral arms or fingers extending laterally and/or inwardly from the shuttle spine 160. The shuttle fingers 156 can extend laterally, downwardly, and medially with respect to the shuttle spine 160, as shown. The shuttles 14 can have slits 20 or shuttle lateral slots 158 between the shuttle fingers 156. The shuttle fingers 156 can be flexible or rigid.

The shuttle 14 can have a shuttle longitudinal axis 157. The shuttle longitudinal axis 157 can be flat or curved, for example have a shuttle radius of curvature 154 from about 3 mm to about 5 mm, more narrowly from about 3 mm to about 4 mm, for example about 3.5 mm.

The shuttle spine 160 can be flexible or rigid. The shuttle 14 can be made from a single panel of material (e.g., metal), for example by bending and laser cutting the panel.

The suture holders 18 can be one, two or more circular, oval, or otherwise elongated, longitudinal slots in the shuttle spine 160. For example, the suture 70 can extend through one or both suture holders 18. The suture 70 can be fused to the shuttle 14 adjacent to the suture holders 18. A detachable or fixed frame can be attached to the slots in the shuttle 14 and the suture 70 can be attached to the detachable frame. For example, the detachable frame can be an arc-shaped wire attached at a first end to a first slot in the shuttle spine 160 and at a second end to the adjacent second slot in the shuttle spine 160.

Figure 13A:
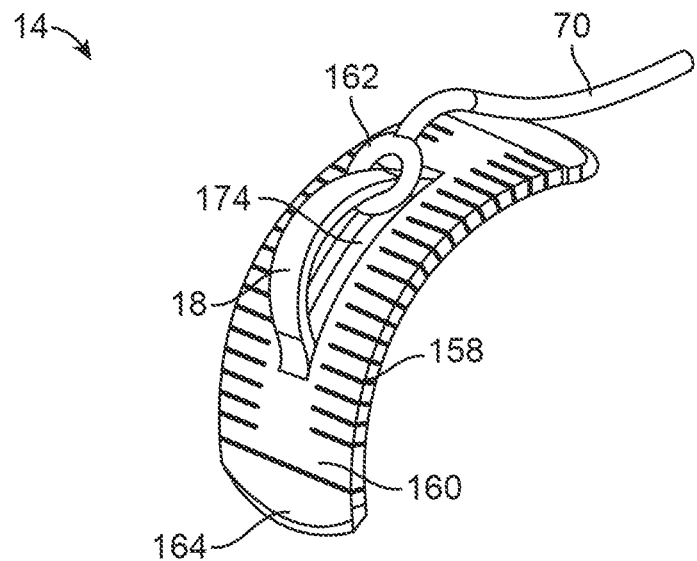
FIGS. 13a and 13b illustrate variations of the shuttle.

FIG. 13a illustrates that the suture holder 18 can be an arc integral with the shuttle spine 160. For example, the shuttle 14 can be made from a single panel of material (e.g., metal). The lateral sides of the suture holder 18 can be cut, and the longitudinal ends can remain integrated with the shuttle spine 160. The suture holder 18 can then be bent or otherwise deformed away from the plane of the shuttle spine 160, for example forming an arc away from the plane of the shuttle spine 160.

The suture 70 can have a suture loop 162 at the terminal end of the suture 70. The suture loop 162 can extend around and completely or partially circumscribe the suture holder 18. The remainder of the suture 70 can be integral with the suture loop 162, or can removably attached to the suture loop 162. The suture loop 162 can be circular or oval.

Figure 13B:
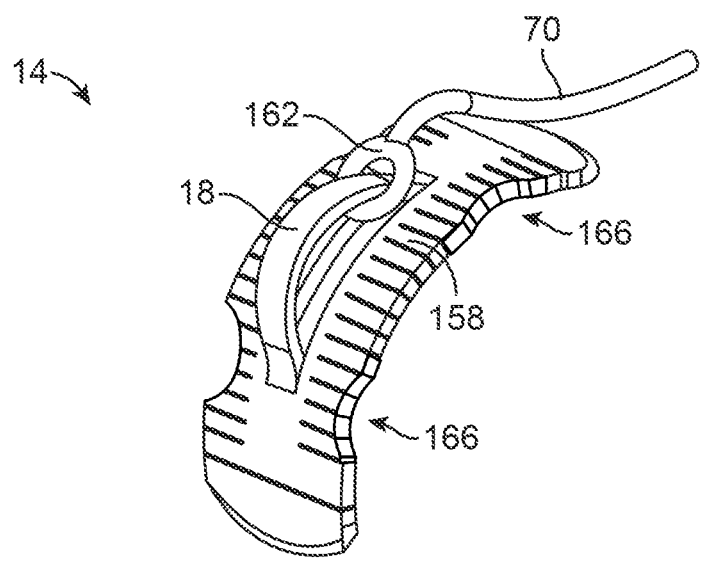
Figure 25A:
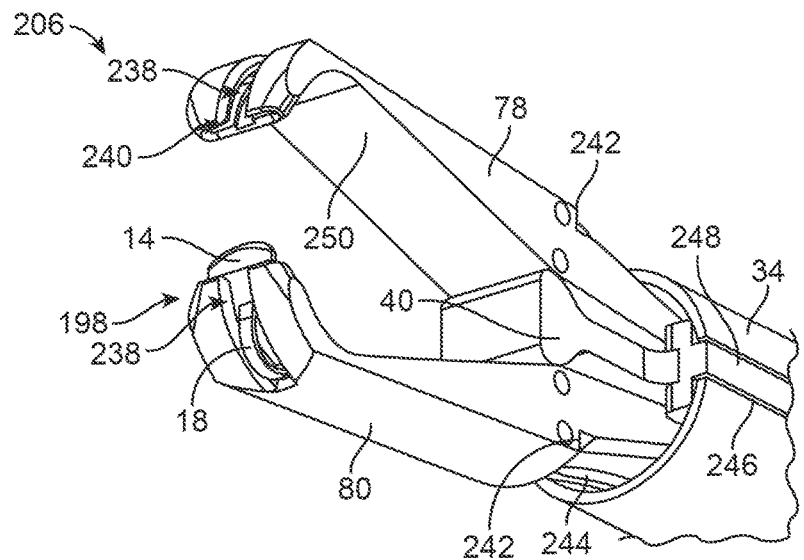
Figure 25B:
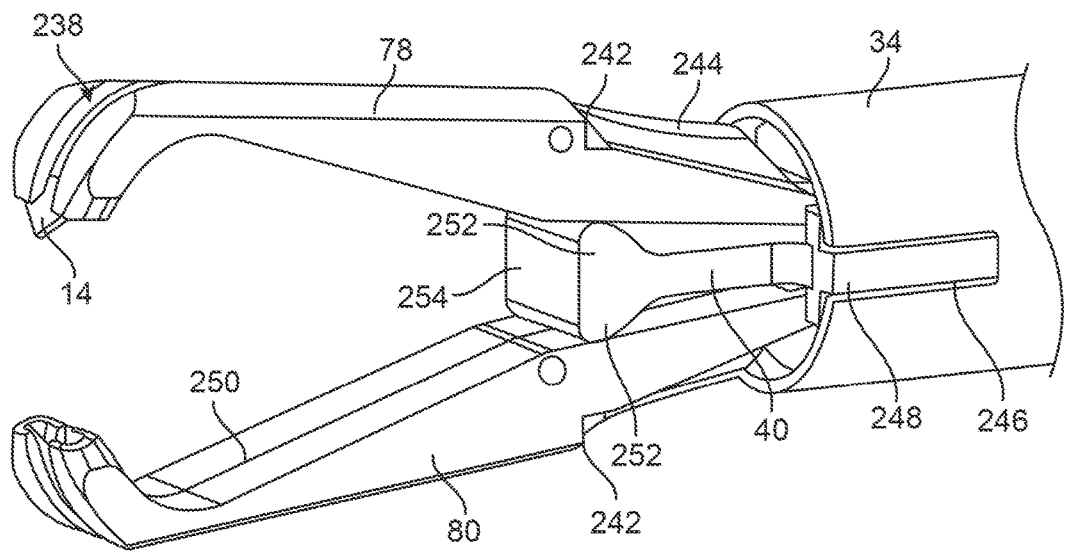
Figure 25C:
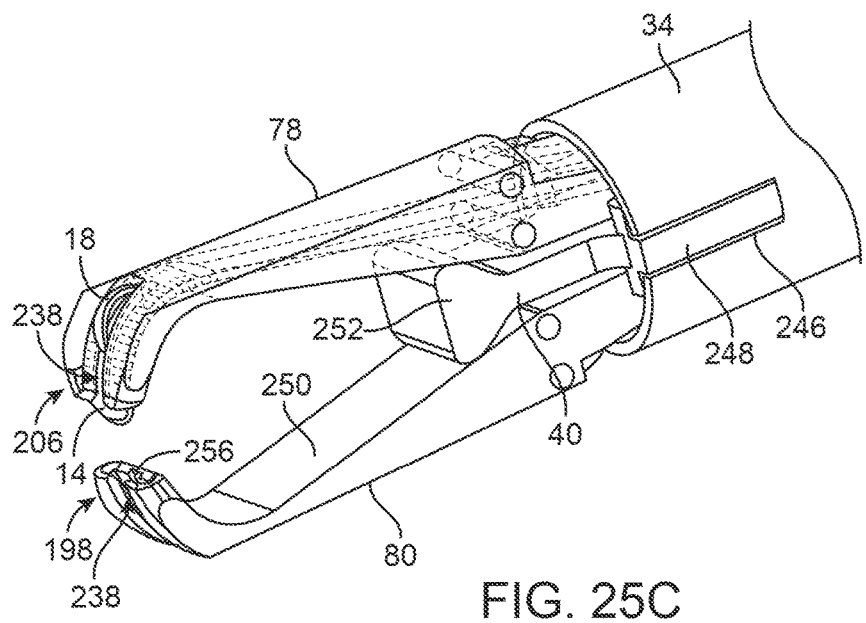
Figure 25D:
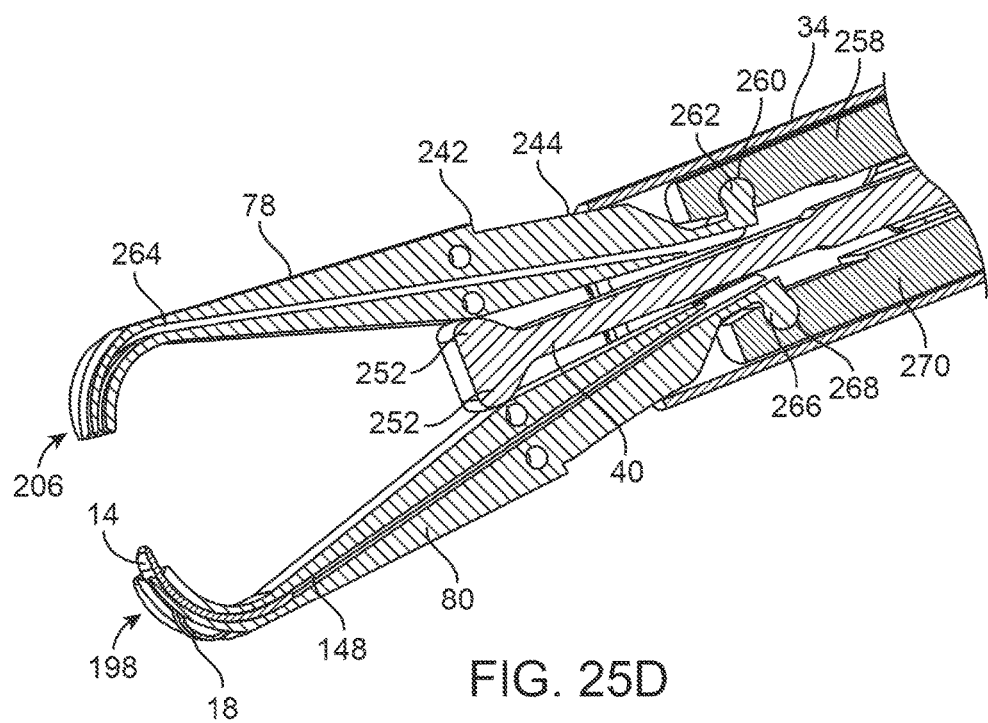
Figure 26A:
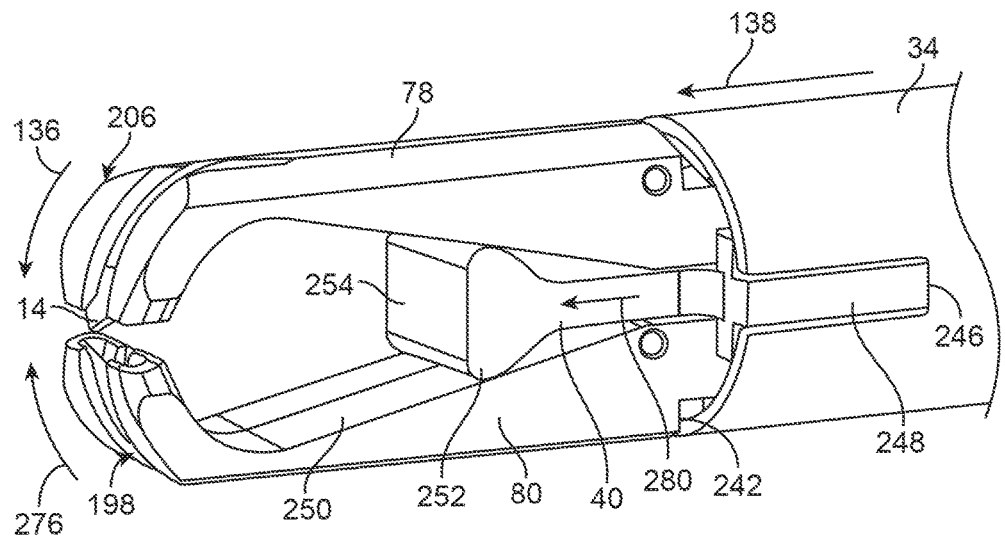
FIG. 26a is a side perspective view of a variation of the distal end of device with the jaws in a closed configuration with the shuttle in the upper jaw and not engaged in the lower jaw.
Figure 26B:
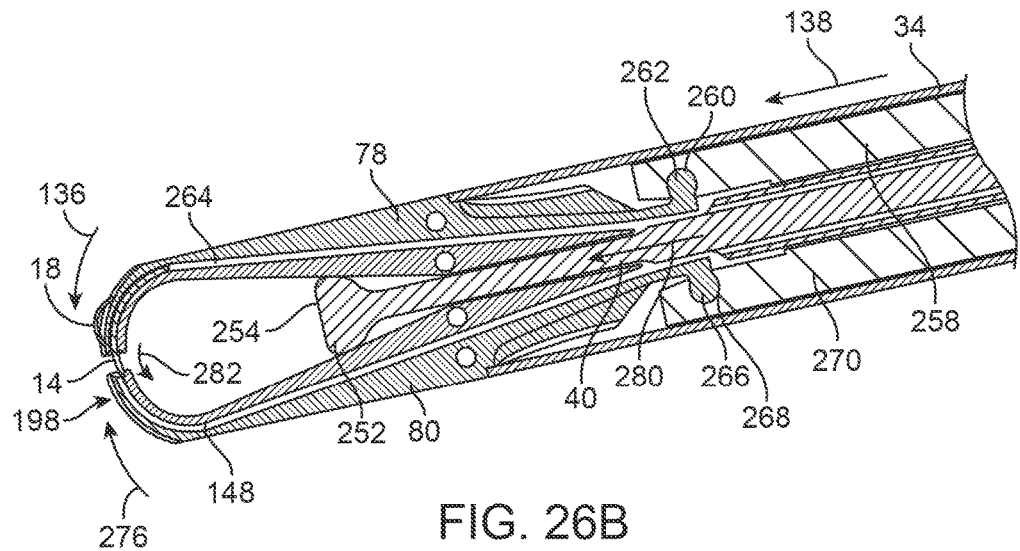
FIGS. 26b and 26c are longitudinal cross-section and side perspective views, respectively, of the device of FIG. 26a with the shuttle in the top and bottom jaws.
Figure 26C:
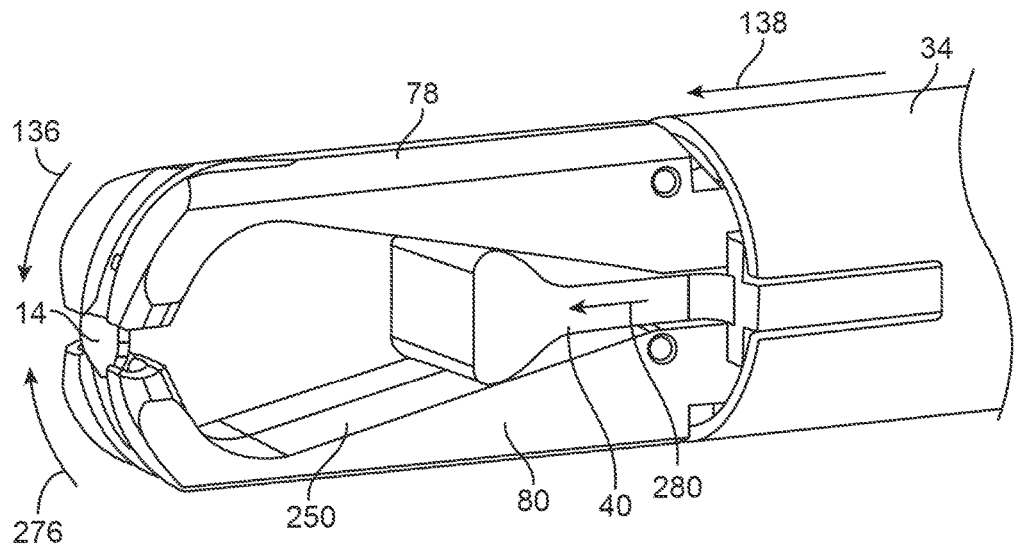
Figure 26D:
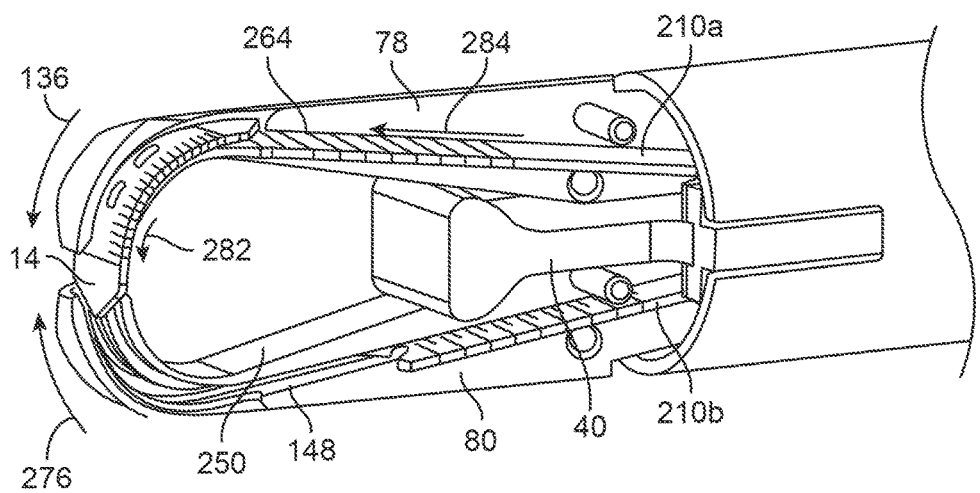
FIG. 26d is a partial cut-away view of FIG. 26c.

FIG. 13b illustrates that the shuttle 14 can have one or more shuttle notches 166 or cut-outs. For example, the shuttle 14 can have two shuttle notches 166 on each lateral site of the shuttle. The shuttle notches 166 can be even longitudinally spaced and distributed along the shuttle 14. The shuttle notches 166 can be curved. The sides of the shuttle 14, other than at the notches, can be straight.

A radius of curvature of the shuttle notch 166 can be from about 1 mm to about 2 mm.

FIGS. 14a through 14c illustrate that one or both of the longitudinally terminal ends of the shuttle 14 can be curved or sharpened shuttle tips 164. For example, the shuttle tip 164 can have an angled chisel tip or needle tip.

The shuttle holder can have a holder leader 170 extending away from the shuttle spine 160. The end of the holder leader 170 away from the shuttle spine 160 can be a closed wire loop 98 configured to attach to the suture 70. A loop neck 172, such as a dual clamp, can fix a first terminal end of the leader wire to an intermediate point on the holder leader 170, as shown. A second terminal end of the holder leader 170 can extend through the shuttle longitudinal slot 174 and terminate at a leader anchor 168 such as a crimp or swaged ball or disc having a larger diameter than the width of the shuttle longitudinal slot 174, for example to slidably attach the suture holder 18 to the shuttle longitudinal slot 174. The suture holder 18 can be slidably captured in the shuttle longitudinal slot 174 by the leader anchor 168.

The holder leader 170 can be translatably and/or rotationally fixed in the shuttle longitudinal slot 174 or can slide and/or rotate in the shuttle longitudinal slot 174. For example, the wire loop 98 can extend past a first end of the shuttle spine 160 when the shuttle 14 is being translated in a first direction (e.g., toward the lower jaw 80 from the upper jaw 78), and the holder leader 170 can passively rotate and translate when the shuttle 14 is then translated in a second direction (e.g., toward the upper jaw 78 from the lower jaw 80).

The holder leader 170 can be rigid or flexible. For example, the holder leader 170 can be made from stainless steel, other material disclosed herein, or combinations thereof.

The suture 70 can be passed through and/or tied to the wire loop 98. The wire loop 98 can be at a height away from the shuttle spine 160. The wire loop 98 can extend proximally or distally past the end of the shuttle tip 164. For example, the suture 70 can be attached to the wire loop 98 away from sharp edge sharps to minimize the risk of cutting or damaging the suture 70.

FIGS. 15a and 15b illustrate that suture 70 can be directly attached or fused to the shuttle spine 160 at a suture attachment 176 in the longitudinal and lateral middle of the shuttle 14. The suture 70 can be braided.

For example, the entire shuttle 14 can be made from plastic and can be molded, overmolded, or otherwise joined to a plastic suture. The suture can be thermally formed to the shuttle 14. The suture 70 can extend through the shuttle 14, for example at a suture anchor 178. The suture anchor 178 can be the terminal end of the suture 70 extending through and attached to the shuttle 14.

FIGS. 16a and 16b illustrate that the leader or wire loop 98 can extend partially or entirely in a plane perpendicular to the plane of the shuttle spine 160. A first terminal end of the wire loop 98 can have a leader first anchor 184. A second terminal end of the wire loop 98 can have a leader second anchor 186. The shuttle spine 160 can have a shuttle longitudinal first slot 180 and a shuttle longitudinal second slot 182. The shuttle longitudinal slots 174 can be elongated or circular. The wire loop 98 can be made from Nitinol and/or steel, for example, and can be tied to the suture.

The wire loop 98 can extend through the shuttle longitudinal slots 174. The leader first and second anchors can be on the underside (e.g., the concave side or radially interior side) of the shuttle spine 160. The wire loop 98 can be on the outerside (e.g., the convex side or radially exterior side) of the shuttle spine 160. Neither, one, or both of the leader anchors 168 can be fixed or integrated (e.g., melted or welded) to the shuttle spine 160. Neither, one or both of the leader anchors 168 can be slidably attached to the longitudinal slots. The wire loop 98 can be fixed or slide longitudinally with respect to the shuttle spine 160.

The wire loop 98 can have a longitudinally symmetric or assymetric (as shown) shape. For example, the wire loop 98 can be an arc (similar to the shape shown by the suture holder 18 in FIGS. 13a and 13b) or can asymmetrically overhang (as shown) toward one of the ends of the longitudinal shuttle.

FIG. 17a illustrates that the device 188 can have the shuttle 14 in a position spanning across the upper jaw 78 and the lower jaw 80. The jaws can have jaw lateral ridges 190. The shuttle fingers 156 can wrap around the jaw lateral ridges 190, for example, slidably attaching the shuttle to the jaws. The jaw lateral ridges 190 at the terminal ends of the upper 78 or top jaw 30 and the bottom or lower jaw 80 can align when the jaws are in a closed configuration, for example so the shuttle 14 can slide along a continuous ridge between the upper 78 and lower jaws 80.

FIG. 17b illustrates that the device 188 can have a lower pusher 76 slidably attached to the jaw lateral ridge 190 on the lower jaw 80. The lower pusher 76 can abut the shuttle 14.

FIG. 17c illustrates that the device 188 can have an upper pusher 86 slidably attached to the jaw lateral ridge 190 on the upper jaw 78. The upper 86 and/or lower pushers 76 can be shaped like the shuttle 14. The shuttle 14 can be pushed onto a straight length of the lower jaw 80. The shuttle 14 can deform to a straight configuration when on a straight length of the jaws and to a curved configuration when on a curved length of the jaws.

The pushers can be generally shaped similarly to the shuttles 14, having fingers, longitudinal slots, spines and lateral slots between the fingers. More than one pusher can be used concurrently on a single device 188 (e.g., if the pushers in FIGS. 17b through 17d were shuttles 14 and if additional pushers were used), for example to deliver multiple sutures 70 to the same target site.

FIG. 17d illustrates that the shuttle 14 can be pushed, as shown, to the upper jaw 78 by the lower pusher 76. The lower pusher 76 can then retreat onto the lower jaw 80.

FIGS. 18a and 18b illustrate that the upper and/or lower jaws 80 can each have jaw spines 208. The jaw spines 208 can extend medially from the remainder of the jaws toward (as shown) or away from the jaw control extension longitudinal axis. For example, the jaws spines can extend from the remainder of the jaws distally until the terminal distal ends 2 of the jaws, distal to where the jaws extend into a medially-curved jaw medial extension closer to and in the respective jaw tip from a jaw longitudinal extension 191, 202.

The jaws can have jaw lateral ridges 190 or rails 16, as described elsewhere herein. The jaws can have a T-shaped cross-section.

The shuttle 14 can have shuttle fingers 156 that can each have a shuttle downward extension 196. The shuttle finger 156 can each have a shuttle lateral extensions 192 extending laterally from the respective shuttle spine 160. The shuttle fingers 156 can have shuttle downward extensions 196 that can each extend downward (e.g., toward the longitudinal axis of the jaw structure) from the laterally terminal ends of the lateral extensions. The shuttle fingers 156 can have shuttle inward extensions 194 that can extend inward from the shuttle downward extensions 196. The shuttle spines 160 and/or lateral extensions, downward extensions, and inward extensions can slidably wrap around the jaw lateral ridges 190.

The upper jaw tip 206 and/or lower jaw tip 198 can have blunt, beveled (e.g., needle-tip), chisel (e.g., beveled on opposite sides, as shown in FIGS. 18a and 18b), conical, Sprotte, diamond, Tuohy tips, or combinations thereof (e.g., the upper jaw tip 206 can have a first tip shape and the lower jaw tip 198 can have a second tip shape). The bevel on the distal side of the jaw tips can have the same angle and length, or a smaller angle and longer length than the bevel on the proximal side of the jaw tips.

The upper jaw tip 206 can have a tip gap 290 or touch the lower jaw tip 198 when the jaws are in a closed configuration.

FIGS. 19a and 19b illustrate that the jaw spines 208 in one or both jaws can terminate before the respective jaw tips or jaw medial extensions.

The bevel on the proximal side of the jaw tips can have a smaller angle and longer length than the bevel on the distal side of the jaw tips.

FIGS. 20a and 20b illustrate that the jaw spine 208 on the upper jaw 78 can extend along the straight length of the upper jaw 78 and can terminate at or proximal to the upper jaw medial extension 204 or upper jaw tip 206. The jaw lateral ridge 190 on the upper jaw 78 can extend to the terminal distal tip of the upper jaw 78.

The jaw spine 208 on the lower jaw 80 can extend to the terminal distal tip of the lower jaw 80.

The jaw lateral ridge 190 on the lower jaw 80 can extend along the straight length of the lower jaw 80 and can terminate at or proximal to the lower jaw medial extension 200 or lower jaw tip 198.

When the jaws are in a closed configuration, the lower jaw tip 198 can be positioned proximally to and overlap the upper jaw tip 206. The upper jaw tip 206 and lower jaw tip 198 can overlap along a tip interface 211. For example, the distal end 2 of the jaw spine 208 on the lower jaw 80 can overlap and slide against the proximal side of the upper jaw tip 206. The upper jaw tip 206 can contact the lower jaw tip 198 at the tip interface 211 or there can be a gap between the upper jaw tip 206 and the lower jaw tip 198 at the tip interface 211.

The tip interface 211 can have a tip interface axis 214 with respect to the jaw structure longitudinal axis 42. The tip interface axis 214 can intersect the jaw structure longitudinal axis 42 at a tip interface angle 212 of about 90°.

The upper jaw tip 206 can be distal to the lower jaw tip 198 at the tip interface 211.

The distal terminal end of the jaw lateral ridge 190 of the upper jaw 78 can contact or not contact the distal terminal end of the jaw lateral ridge 190 of the lower jaw 80 when the jaws are in a closed configuration.

FIGS. 21a and 21b illustrate that the tip interface 211 can have a tip interface axis 214 with respect to the jaw structure longitudinal axis 42. The lower jaw tip 198 can be distal to the upper jaw tip 206 at the tip interface 211. The tip interface angle 212 can be from about 30° to about 60°, more narrowly 30° to about 45°, for example about 35°.

FIGS. 22a through 22c illustrate that the distal end 2 of the lower jaw tip 198 (as shown) or upper jaw tip 206 can have a tip seat 216. The tip seat 216 can be shaped to receive the shape of the opposite jaw tip. For example, the tip seat 216 can be triangular (e.g., A-shaped or V-shaped).

The tip seat 216 can surround the lateral sides and distal side of the upper jaw tip 206 when the jaws are in a closed configuration. The tip seat 216 can contact or not contact (i.e., there can be a gap) the upper jaw tip 206 when the jaws are in a closed configuration.

The jaw lateral ridge 190 of the jaw with the tip seat 216 (the bottom jaw 38, as shown) can extend to the terminal end of the lower jaw tip 198 and the tip seat 216. The jaw lateral ridge 190 of the jaw opposite of the tip seat 216 (the upper jaw 78, as shown) can narrow, for to a point at the terminal end of the respective jaw tip. The narrowed jaw lateral ridge 190 can be received within the tip seat 216.

FIGS. 23a and 23b illustrate that the upper 78 and/or lower jaws 80 can have circular or oval cross-sections. The upper 78 and/or lower jaws 80 can be made from solid or hollow rods, for example having a diameter of from about 0.030 in. to about 0.100 in., for example about 0.060 in.

The terminal end of the upper and/or lower jaw tip 198 can have a conical shape. The terminal end of the lower jaw tip 198 can have an tip seat 216 that can be inverse or negative to a conical shape, for example sized and shaped to receive the upper jaw tip 206.

The shuttle 14 can have a circular or oval cross-section.

The pushers can have pusher fingers 219 extending from the pusher spine 218, similar to the shuttle fingers 156 and shuttle spine 160. The pusher fingers 219 can be triangular.

FIGS. 24a through 24c illustrate that the distal end 2 of the device 188 can be inserted into a cannula 226, for example to be deployed percutaneously through a cannula 226 inserted in a patient at a target site. The cannula 226 can have a cannula inner diameter 228. The cannula inner diameter 228 can be from about 4 mm to about 8 mm, for example 7 mm, or 6.86 mm (0.270 in.), or 15 French gauge (5 mm (0.197 in.)).

The shuttle 14 can have a shuttle height 220. The shuttle height 220 can be from about 0.020 in. to 0.060 in., for example about 0.041 in.

The compression cover 34 can be attached to or integral with one or more jaw control extensions 40. For example the jaw control extensions 40 can extend from the lateral distal ends 2 of the compression cover 34. The jaw control extension 40 can slidably attach to or contact the jaws directly or indirectly. The jaw control extension 40 can push the jaws apart from each other when the jaw control extension 40 is translated proximally with respect to the jaws, and toward each other when the jaw control extension 40 is translated distally with respect to the jaws.

One or more upper cam pins 222 can extend laterally from the one or both lateral sides of the proximal end of the upper jaw 78. One or more lower cam pins 232 can extend laterally from the one or both lateral sides of the proximal end of the lower jaw 80 at the same or different longitudinal position as the upper cam pins 222.

The jaw control extensions 40 can have one or more upper cam slots 230 and one or more lower cam slots 224. The upper 230 and/or lower cam slots 224 can be straight, curved, angled (as shown) or a combination thereof. The cam pins can be positioned inside and through the respective cam slots. The cam pins can slide within the cam slots.

When the jaw control extension 40 is translated distally with respect to the jaws, the cam pins can slide proximally within the respective cam slots and rotate the jaws away from each other. When the jaw control extension 40 is translated proximally with respect to the jaws, the cam pins can slide distally within the cam slots and rotate the jaws toward each other.

The jaws can have a jaw extension length 234. The jaw extension length 234 can be the length from the distal end 2 of the jaw control extension 40 to the proximal side of the jaw tips. The jaw extension length 234 when the jaws are in a closed configuration can be from about 5 mm to about 30 mm, for example about 16 mm and 15.95 mm.

The jaws can have a jaw straight gap 236 along the straight length of the jaws. The jaw straight gap 236 can be from about 1 mm to about 3.5 mm, for example about 1.1 mm or about 3.2 mm. For example, the cannula inner diameter 228 can be 5 mm and the jaw straight gap 236 can be about 1.1 mm.

The jaws can be separate or can be integrated at a jaw body. Jaws integrated in a jaw body can rotatably deform away from each other when moved into an open configuration.

FIGS. 25a through 25f illustrate that the upper jaw tip 206 and/or lower jaw tip 198 can have suture holder slots 238. The suture holder slots 238 can extend medially along the outer surface of the respective jaw tip. The suture holder slot 238 can extend from the outer surface of the jaw tip to the respective track. The suture holder 18 can be accessible through or extend out of the suture holder slot 238. The suture 70 (not shown) can attach to or be integral with the suture holder 18 in or outside of the suture holder slot 238.

The upper track 264 can distally terminate at an upper jaw tip shuttle port 240. The lower track 148 can distally terminate at a lower jaw tip shuttle port 256. The shuttle 14 can extend out of or into, and pass through each of the shuttle 14 ports. During use, the sharpened shuttle tip 164 extending out of the shuttle port can pierce, cut and dissect tissue 74 when the jaws are rotated to a closed configuration.

The upper jaw 78 and % or lower jaw 80 can have a jaw stop 242. The jaw stop 242 can be a feature, shape or configuration that can abut and stop the distal translation of the compression cover 34 with respect to the jaws. For example, the distal terminal end of the compression cover 34 can abut the jaw stops 242 when the jaws are in a closed configuration.

The radially inner surface of the jaws can have radially inner slopes 250.

The upper jaw 78 and/or lower jaw 80 can have a jaw slide 244. The jaw slide 244 can be a radially outer surface of the jaws between the jaw stops 242 and the compression cover 34 when the compression cover 34 is in a proximally retracted 126 position with respect to the jaws and/or the jaws are in an opened configuration. The jaw slide 244 can increase in radius from the jaw structure longitudinal axis 42 in the distal longitudinal direction (e.g., the larger the longitudinal dimension of the jaw slide 244, the larger the radial dimension of the jaw slide 244). When the compression cover is translated distally 138 with respect to the jaws, the radially inner distal edge of the compression cover 34 can slide along the jaw slide 244, and press the jaw slide 244 toward the jaw structure longitudinal axis 42. A radially compressive force delivered from the compression cover 34 to the jaw slide 244 can create a torque in the respective jaw, rotating the respective jaw toward the jaw structure longitudinal axis 42 and the opposing jaw.

The device 188 can have a jaw control extension 40. The jaw control extension 40 can extend along the jaw structure longitudinal axis 42. The jaw control extension 40 can extend between the jaws proximal to the jaw tips. The jaw control extensions 40 can terminate in a jaw control extension head 254.

The jaw control extension head 254 can have one or two lobes or cams. Each lobe can extend from the longitudinal axis of the jaw control extension 40 toward a jaw. The lobes can act similarly to the opening roller ball shown in FIGS. 4a, 4d, and elsewhere herein. The upper jaw 78 and lower jaw 80 can have upper and inner jaw radially inner slopes 250, respectively. The inner slopes can be the radially inner surfaces of the jaws proximal to the jaw tips and distal to the jaw control extension head 254 when the jaw control extension head 254 is in a proximally retracted position with respect to the jaws. The radially inner slope 250 can increase in radius from the jaw structure longitudinal axis 42 in the distal longitudinal direction (e.g., the larger the longitudinal dimension of the radially inner slope 250, the larger the radial dimension of the radially inner slope 250). When the jaw control extension 40 is proximally translated or retracted with respect to the jaws, the lobes can slide against the radially inner slopes 250 of the jaws and press the jaws away from each other into an open configuration.

When the jaws are in an open configuration, the compression cover 34 can be positioned at or proximally past the proximal end of the jaw slides 244, and the jaw extension head can be positioned at or proximally past the proximal end of the radially inner slopes 250.

The jaw control extension 40 can be attached to or integral with a control rail 248. The control rail 248 can extend radially from one or both lateral sides of the jaw control extension 40, for example in a plane at a right angle to a plane defined by the opposing jaws or the opposing extension head lobes 252.

The compression cover 34 can have a control rail slot 246. The control rail slot 246 can extend to the distal terminal end of the compression cover 34. The control rail 248 can be fixed to or longitudinally translate within the control rail slot 246. The control rail 248 can interference fit, abut or stop against the proximal end of the control rail slot 246, for example when the control rail 248 is in a proximal or distal longitudinal position with respect to the jaws. The control rail 248 can move longitudinally in unison (i.e., coincidentally) with the compression cover 34 in the distal and/or longitudinal directions. The control rail 248 can move longitudinally in unison with the jaw control extension 40 in the distal and/or longitudinal directions.

The device 188 can have an upper socket arm 258 and a lower socket arm 270 radially inside of the compression cover 34. The upper socket arm 258 and lower socket arm 270 can be a single integrated element (e.g., a hollow cylinder) or separate elements. The upper socket arm 258 can be opposite the lower socket arm 270. The upper socket arm 258 can be translatably fixed (i.e., mechanically attached to translate in unison) to the lower socket arm 270. The jaw control extension 40 can extend longitudinally between the upper 258 and lower socket arms 270 or within a hollow channel inside a unitary socket arm (comprising the upper 258 and lower socket arms 270 as an integrated element). The distal terminal ends of the socket arms can extend to or proximal to the distal terminal end of the compression cover 34 when the jaws are in an open configuration.

The proximal terminal end of the upper jaw 78 can have a laterally elongated upper jaw bearing 262. The upper jaw bearing 262 can extend radially outward from the remainder for the proximal end of the upper jaw 78.

The distal end 2 of the upper socket arm 258 can have a laterally elongated upper jaw socket 260. The upper jaw socket 260 can open medially and have a diameter approximately equal to or slightly larger than the diameter of the upper jaw bearing 262.

An upper jaw 78 hinge can have the upper jaw bearing 262 and the upper jaw socket 260. The upper jaw 78 can rotate around the transverse axis of the upper jaw bearing 262. The upper jaw bearing 262 can rotate in the upper jaw socket 260.

The proximal terminal end of the lower jaw 80 can have a laterally elongated lower jaw bearing 266. The lower jaw bearing 266 can extend radially outward from the remainder for the proximal end of the lower jaw 80.

The distal end 2 of the lower socket arm 270 can have a laterally elongated lower jaw socket 268. The lower jaw socket 268 can open medially and have a diameter approximately equal to or slightly larger than the diameter of the lower jaw bearing 266.

A lower jaw 80 hinge can have the lower jaw bearing 266 and the lower jaw socket 268. The lower jaw 80 can rotate around the transverse axis of the lower jaw bearing 266. The lower jaw bearing 266 can rotate in the lower jaw socket 268.

The upper 86 and/or lower pushers 76 can have entire lengths or only distal ends 2 that can have articulated segmentations 286. The articulated segments 286 can rotate with respect to each other around an axis perpendicular to the longitudinal axis of the respective pusher. The articulated segmentations 286 can be connected by a discrete hinge (e.g., a pin or snap connection) or can be longitudinally coincidental or longitudinally alternating lateral slots cut into the sides of the pusher, similar to the shape of the shuttle lateral slots 158. The proximal end of either or both upper 86 and lower pushers 76 can have a continuous, non-segmented, flat, uniform ribbon of material.

Each of the upper 86 and/or lower pushers 76 can have distal terminal ends that can have a shuttle seat 274. The shuttle seat 274 can be an inverse shape to the shape of the shuttle tip 164. For example, if the shuttle tip 164 has an angled end, the shuttle seat 274 can have the opposite angle. If the shuttle tip 164 has a convex curved end, the shuttle seat 274 can have a concave curved end with the same radius of curvature as the shuttle tip 164.

FIGS. 26a through 26d illustrate that the compression cover 34 can be distally translated, as shown by arrow, with respect to the jaws. The compression cover 34 can deliver translational force through the edges of the control rail slot 246 to the control rail 248. The control rail 248 can deliver the translational force to the jaw control extension 40. The jaw control extension 40 can translate distally, as shown by arrow, concurrently with the compression cover 34. The compression cover 34 can translate 138 over the jaw slides 244, pressing radially inward on the jaw slides 244. The jaw control extension head 254 can move distally with respect to the jaws, as shown by arrow 280, for example, allowing the closure of the jaws without interference fitting or abutting against the jaw control extension head 254. The upper jaw 78 and/or lower jaw 80 can rotate radially inward, as shown by arrows.

When the jaws are in a closed configuration, the compression cover 34 can be positioned at or adjacent to the jaw stop 242, and the jaw extension head can be positioned at or proximally past the proximal end of the radially inner slopes 250.

When the jaws are in a closed configuration, if the shuttle 14 is in the upper track 264, the upper pusher 86 can translate distally through the upper track 264. The distal terminal end of the upper pusher 86 can abut the shuttle 14. The upper pusher 86 can then push the shuttle 14 through the upper track 264, out the upper jaw tip shuttle port 240 and into the lower jaw tip shuttle port 256.

When the jaws are in a closed configuration, if the shuttle 14 is in the lower track 148, the lower pusher 76 can translate distally through the lower track 148. The distal terminal end of the lower pusher 76 can abut the shuttle 14. The lower pusher 76 can then push the shuttle 14 through the lower track 148, out the lower jaw tip shuttle port 256 and into the upper jaw tip shuttle port 240.

When the shuttle 14 is pushed from the upper track 264 to the lower track 148 or vice versa, the shuttle 14 can be curvilinearly translated 282, as shown by arrow, following the paths of the upper track 264 and the lower track 148.

When the jaws are in a closed configuration, the shuttle 14 can move from the upper jaw 78 to the lower jaw 80, as shown by arrow, back to the upper jaw 78, and can repeat the motion from the upper jaw 78 to the lower jaw 80, and optionally from the lower jaw 80 to the upper jaw 78 one, two or more times.

The device 188 can have a pusher lockout that can prevent translation of the pushers and the shuttle 14 when the jaws are in an open configuration.

The device 188 can have a jaw lockout preventing opening of the jaws when either of the pushers is extended out of the respective jaw tip shuttle port and/or when the shuttle 14 is concurrently in the upper jaw 78 and the lower jaw 80.

FIG. 27 illustrates that the upper pusher 86 can be distally translated with respect to the jaws. The upper pusher 86 can curvilinearly translate, as shown by arrows 284 and 288, along the upper track 264. The distal terminal end of the upper pusher 86 can exit out of and extend from the upper jaw tip shuttle port 240. The V-shaped (or A-shaped), or curved (e.g., U-shaped) shuttle seat 274 at the distal terminal end of the upper pusher 86 can abut the V-shaped (or A-shaped), or curved (e.g., U-shaped) shuttle tip 164 at the terminal end of the shuttle. The upper pusher 86 can push the shuttle 14 through the upper track 264, across the gap between the upper jaw tip shuttle port 240 and the lower jaw tip shuttle port 256, and into the lower track 148. The shuttle 14 can have a curvilinear translation 282, as shown by arrow, along the tracks.

The lower pusher 76 can have no or one lower pusher articulating segment (as shown), or can have a number of articulating segments, similar to the upper pusher 86 in FIG. 27.

Figure 28:
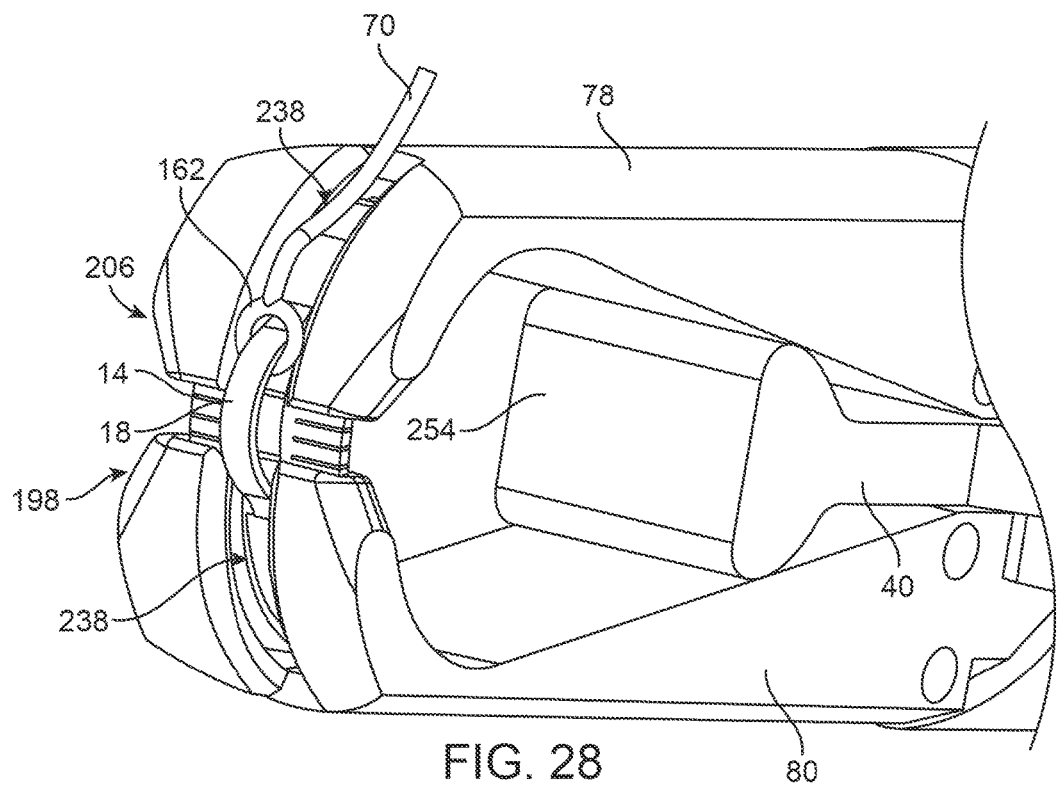
FIG. 28 is a close-up end perspective view of a variation of the device with the shuttle and suture of FIG. 13a or 13b.

FIG. 28 illustrates that the suture 70 can be tied or adhered directly to suture holder 18, for example as shown in FIGS. 13a and 13b. The suture 70 can have a suture loop 162. The suture loop 162 can circumscribe the suture holder 18.

Figure 29:
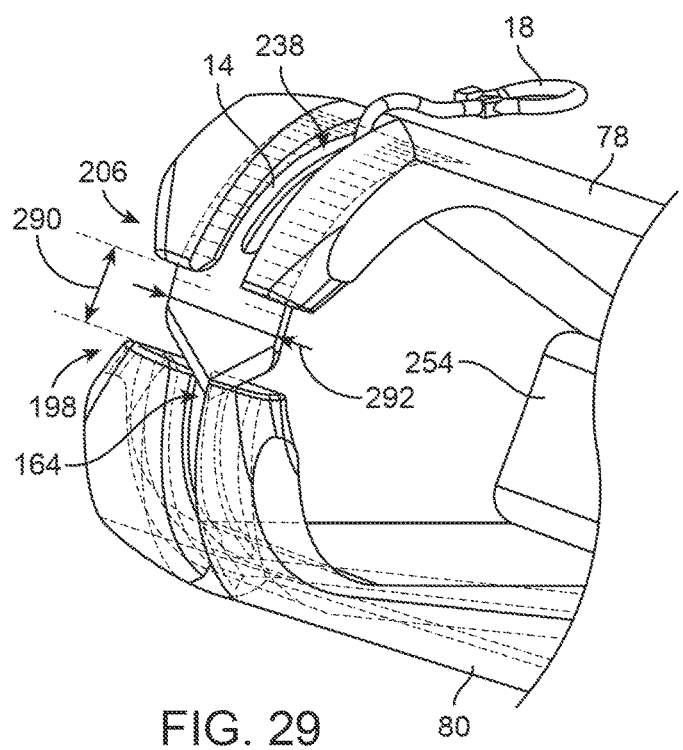
FIG. 29 is a close-up end perspective view of a variation of the device with the shuttle and suture of FIGS. 14a through 14c.

FIG. 29 illustrates that when the jaws are in a closed configuration, the terminal end of the upper jaw tip 206 can be in contact with or have a tip gap 290 to the terminal end of the lower tip jaw. The tip gap 290 can be from about 0 in. to about 0.020 in., for example about 0.008 in.

The shuttle 14 can have a shuttle width 292. The shuttle width 292 can be from about 0.030 in. to about 0.100 in., for example about 0.060 in.

The shuttle 14 can be made from nickel titanium alloys (e.g., Nitinol), stainless steel, other materials disclosed herein, or combinations thereof.

Figure 30A:
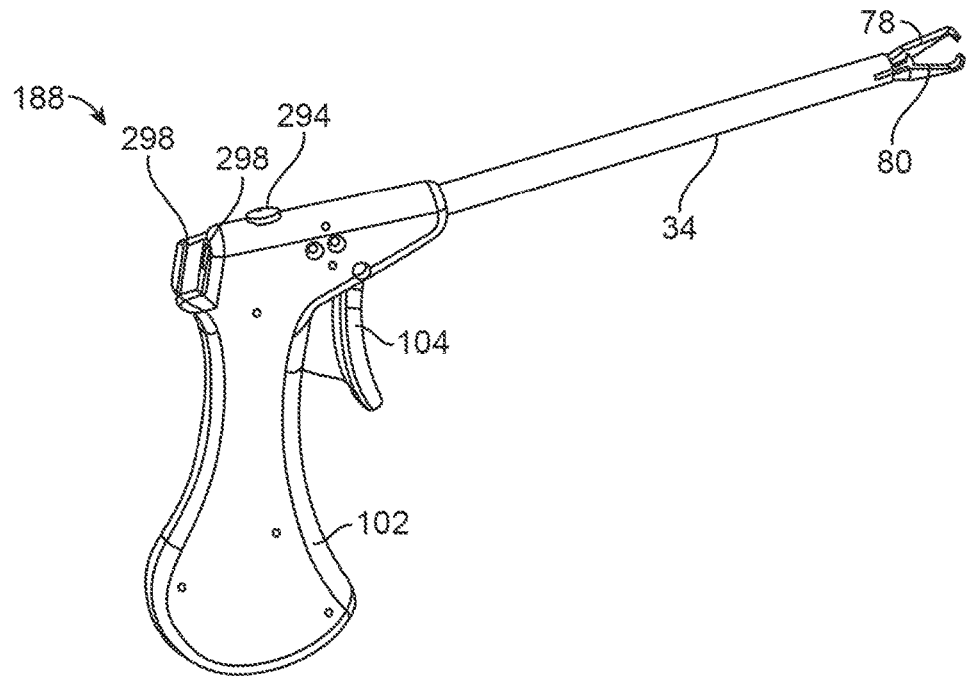
FIGS. 30a and 30b are right rear, and left cut-away views, respectively, of a variation of the device.
Figure 30B:
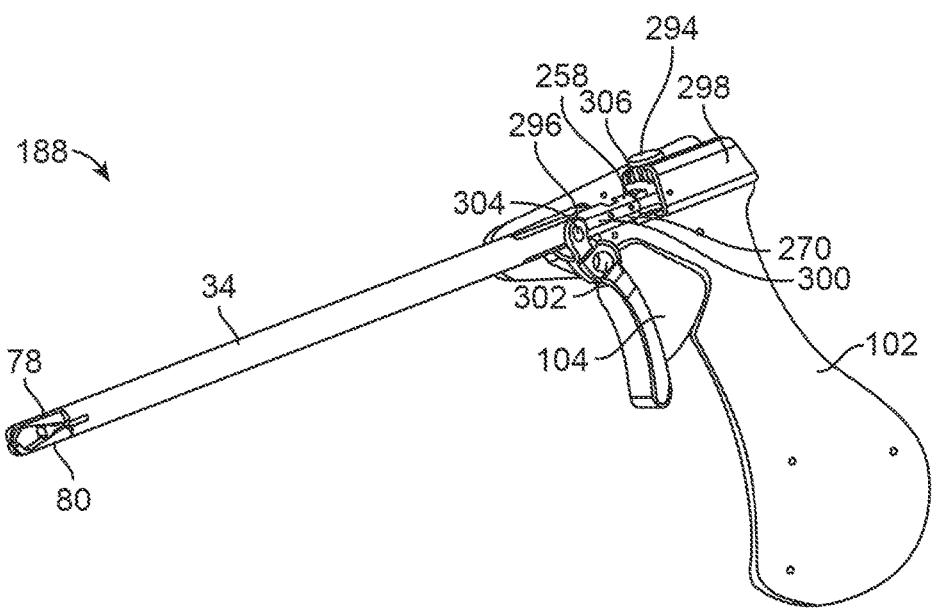
Figure 31:
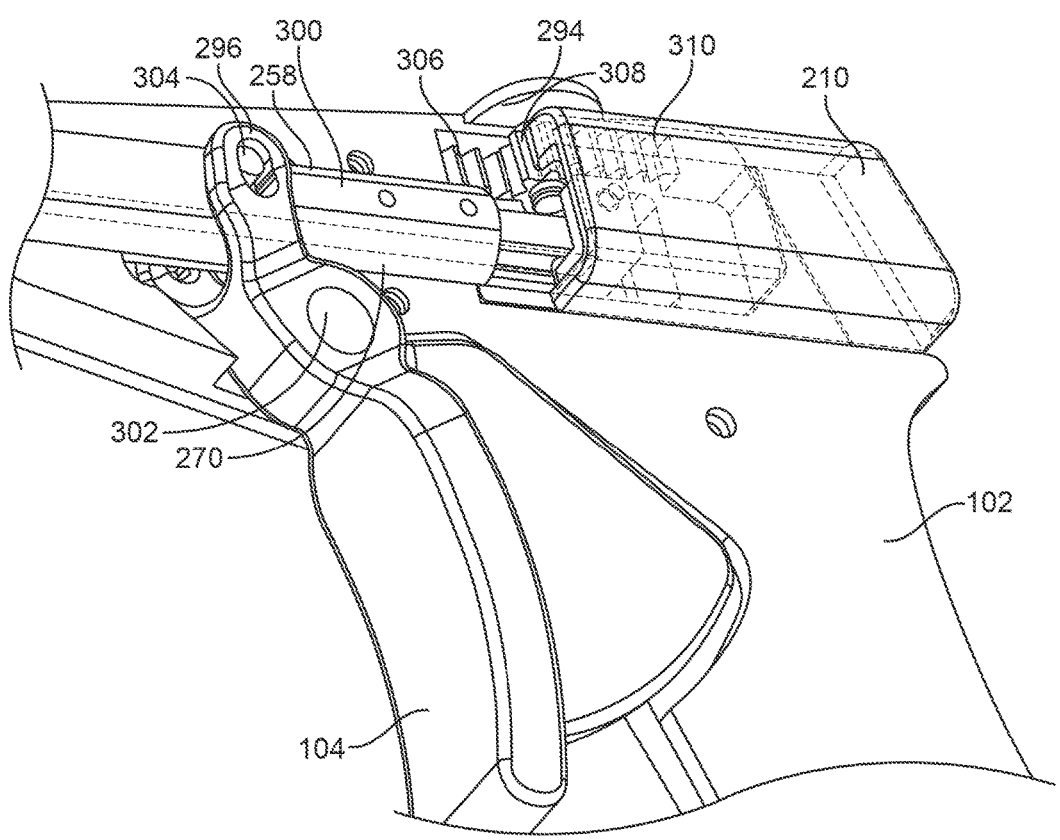
FIG. 31 is a partially cut-away and partially see-through view of the proximal end of a variation of the device.

FIGS. 30a, 30b and 31 illustrate that the lever 106 or handle 104 can control the rotation, and opening and closing of the jaws.

The handle 104 can have a handle pivot 302. The handle pivot 302 can be a rotatable pin joint where the handle 104 can rotatably attach to the base 102. The handle 104 can rotate around the handle pivot 302 with respect to the base 102.

The handle 104 can be attached to the socket arms and/or the compression cover 34 (as shown). For example, the compression cover 34 can have radially and/or laterally extending cover pins 304. The cover pins 304 can attach to the jaw control extension 40. The handle 104 can have one or two transmission ports 314 or loops 296 on opposing lateral sides of the compression cover 34. The cover pins 304 can extend through the transmission loops 296.

The other of the socket arms (as shown) and compression cover 34 not attached to the handle 104 can be attached to the base 102.

Squeezing and rotating the handle 104 toward the base 102 can distally extend 138 the compression cover 34 and jaw control extension 40 with respect to the jaws, or proximally retract 126 the jaws with respect to the compression cover 34 and jaw control extension 40. When the handle 104 is rotated, the jaws can move to an open configuration. For example, when the bottom of the handle 104 is rotated proximally toward the base 102, the transmission loop 296 can rotate distally toward the jaws, pushing the cover pin 304 and the compression cover 34 distally. The transmission loop 296 can force the compression cover 34 and/or jaw control extension 40 to translate distally, for example, closing the jaws.

The proximal end of the upper socket arm 258 and the proximal end of the lower socket arm 270 can be an integral element or can be fixedly attached by a socket arm brace 300.

The terminal proximal end of the upper pusher 86 can attach to or be integrated with an upper pusher 86 shaft and/or upper pusher button 210a. The terminal proximal end of the lower pusher 76 can attach to or be integrated with a lower pusher shaft and/or lower pusher button 210b. The proximal distal ends 2 of the upper pusher button 210a and lower pusher button 210b can be above and below each other or side-by-side (e.g., left and right, as shown). The device 188 can be configured so that pressing (e.g., distally translating) the upper pusher button 210a can distally advance the upper pusher 86, and pressing (e.g., distally translating) the lower pusher button 210b can distally advance the upper pusher 86. Pressing the upper pusher button 210 can proximally retract the lower pusher 76 and/or lower pusher button 210b. Pressing the lower pusher button 210b can proximally retract the upper pusher 86 and/or upper pusher button 210.

The medial sides of the distal ends 2 of the upper and lower pusher buttons 210b can have upper pusher button gears 310 and lower pusher button gears 306, respectively. The upper pusher button gears 310 can face the lower pusher button gears 306.

The pusher toggle knob 294 can be rotatably attached to the base 102. The pusher toggle knob 294 can be integrated or rotationally fixed to a pusher toggle knob gear 308. The pusher toggle knob gear 308 can rotatably interface and interdigitate with the upper pusher button gear 310 on a first side and with the lower pusher button gear 306 on the opposite side of the upper pusher button gear 310.

When the upper pusher button translates distally 284, the upper pusher button gear 310 can rotate the pusher toggle gear, for example also rotating the top of the pusher toggle knob 294 to a position indicating that the upper pusher button 210a has been translated distally 284. The top surface or circumference of the top of the pusher toggle knob 294 can have an indicator, such as an arrow, that can indicate whether the upper pusher 86 or the lower pusher 76 has been translated and by how far, for example indicating the position of the shuttle 14 in the upper track 264, lower track 148, extending out of one track, or extending across both tracks simultaneously. The pusher toggle gear can simultaneously proximally translate the lower pusher button gear 306. For example, when the upper pusher 86 is distally translated, the lower pusher 76 can be simultaneously proximally translated at the same speed.

When the lower pusher button 210b translates distally, the lower pusher button gear can rotate the pusher toggle gear, for example also rotating the top of the pusher toggle knob 294 to a position indicating that the upper pusher button 210a has been translated distally 284. The pusher toggle gear can simultaneously proximally translate the upper pusher button gear 310. For example, when the lower pusher 76 is distally translated, the upper pusher 86 can be simultaneously proximally translated at the same speed.

The pusher toggle knob 294 can be rotated to translate the upper pusher 86 and the lower pusher 76 by transmitting the torque applied to pusher toggle knob 294 through the pusher toggle knob gear 308 and to the upper pusher button gear 310 and/or lower pusher button gear 306 with or without pressing on the proximal terminal ends of the pusher buttons.

Figure 32A:
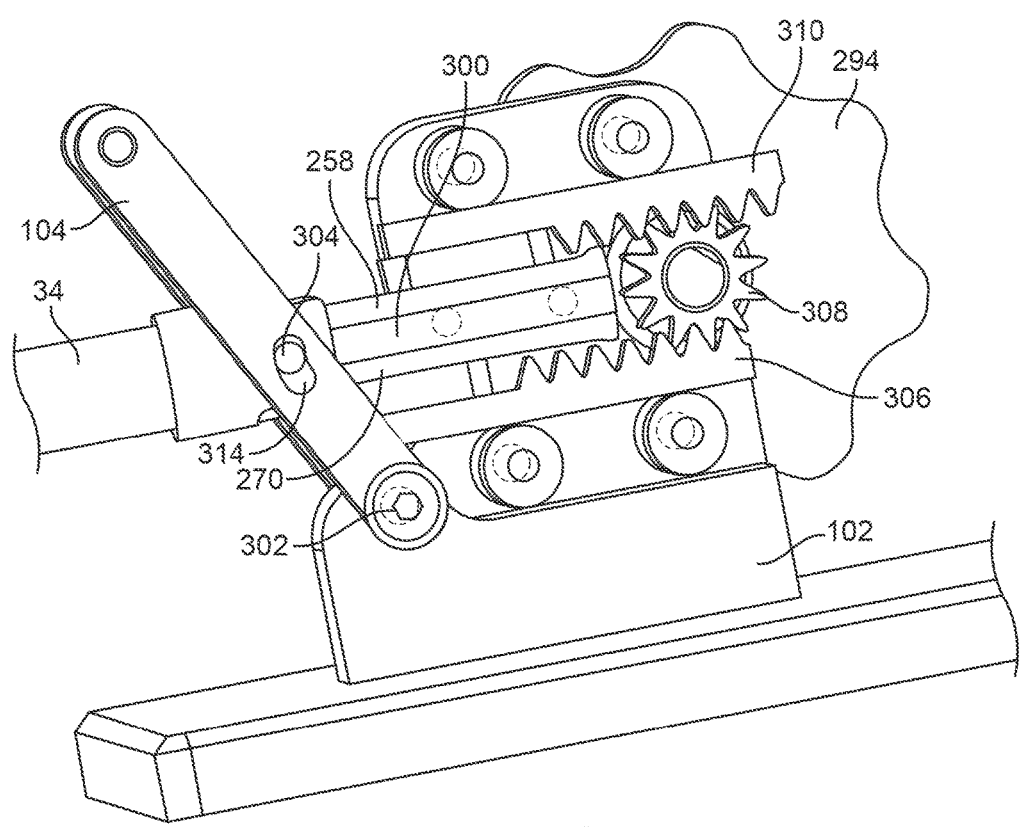
FIGS. 32a and 32b are left and right perspective views of a variation of the pusher drive gears of the device.
Figure 32B:
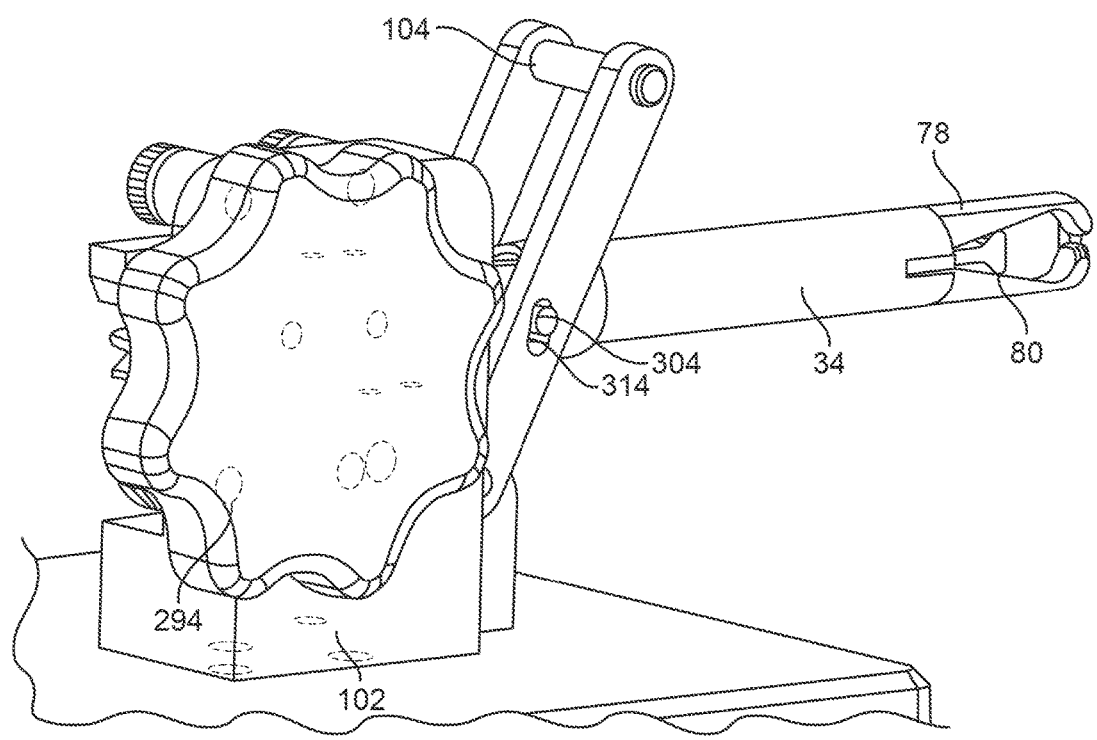

FIGS. 32a and 32b illustrates that the pusher toggle knob 294 can be rotated to translate the upper pusher 86 and the lower pusher 76 by transmitting the torque applied to pusher toggle knob 294 through the pusher toggle knob gear 308 and to the upper pusher button gear 310 and/or lower pusher button gear 306 with or without pressing on the proximal terminal ends of the pusher buttons.

The diameter of the pusher toggle knob 294 can be smaller than the width of the base 102, as shown in FIGS. 30a, 30b and 31, or larger than the width and height of the base 102, and the same size or larger than the handle 104, and the compression cover 34, as shown in FIGS. 32a and 32b.

In a variation of a method of use, the distal end 2 of the device 188 including the jaws can be inserted through a percutaneous cannula 226 when the jaws are in a closed configuration. When the distal end 2 of the device 188 exits the distal end 2 of the cannula 226 at the target site, the handle 104 can be released to rotate away from the base 102. The handle rotation away from the base 102 can move the jaws to an open configuration. The distal end 2 of the device 188 can then be further positioned so the target site is between the upper jaw distal tip 206 and the lower jaw distal tip 198. The handle 104 can then be squeezed to rotate the handle 104 toward the base 102. The handle rotation toward the base 102 can move the jaws into a closed configuration, pinching together tissue 74 at the target site. The shuttle 14 can be completely recessed in the jaw into which the shuttle 14 is loaded, or the shuttle tip 164 can extend out of whichever jaw the shuttle is currently loaded into. The shuttle tip 164 can pierce the tissue 74 as the jaws are closed or after the jaws are closed when the shuttle 14 is translated.

After the jaws are closed, the upper 210a or lower pusher button 210b (e.g., respective to whichever track the shuttle 14 is currently in) can be pressed, distally advancing the respective pusher. The respective pusher can press the shuttle 14 distally, through the gap between the upper 78 and lower jaws 80, if such a gap exists, or directly from one jaw to the other jaw. The shuttle 14 can pull the suture 70 to follow the path of the shuttle 14 or follow a path adjacent to the shuttle 14. When the respective pusher button is fully depressed, the device 188 can emit a sound and/or tactile response (e.g., from a snap or detent in the button or pusher and track) and the pusher toggle knob 294 can have an indicator (e.g., a line or arrow) indicating that the shuttle 14 has been fully translated across the jaws.

The handle 104 can then be rotated away from the base 102. For example, the handle can be released and spring loaded to return to a position rotated away from the base 102. The rotating handle can proximally translate the transmission loop 296. The transmission loop 296 can proximally pull and translate the compression cover 34 and jaw control extension 40, opening the jaws.

The device 188 can then be repositioned so the jaw tips are removed entirely, for example if stitching is complete, or moved adjacent to their previous position in order to place a new stitch. The handle 104 can then be squeezed, closing the jaws. The pusher button of the track in which the shuttle 14 is positioned can then be pressed. The shuttle 14 can then move to the opposite jaw, as described above, pulling the suture 70 through the tissue 74 and forming a stitch.

The above method can be repeated as needed to create a length and position of desired stitches.

Any or all elements of the device 188 and/or other devices 188 or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example), tungsten-rhenium alloys, polymers such as polyethylene teraphthalate (PET)/polyester (e.g., DACRON, from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue 74, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The shuttle 14 throughout the disclosure herein can be attached to a suture 70. Accordingly, the suture 70 can be attached to the shuttle 14 and can follow the movement of the shuttle 14. Similarly, the suture 70 can be attached to and detached from the shuttle 14, for example, attached before and detached after the desired stitching or suturing is complete.

It is apparent to one skilled in the art that various changes and modifications can be made to this disclosure, and equivalents employed, without departing from the spirit and scope of the invention. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A suture manipulating device comprising:
a jaw structure having a longitudinal axis, wherein the jaw structure comprises a first jaw and a second jaw, wherein the first jaw has a first jaw tip and the second jaw has a second jaw tip, wherein the first jaw tip has a tooth and the second jaw tip has a tooth seat configured to receive the tooth, wherein the tooth is configured to interdigitate with the tooth seat when the jaw structure is in a closed configuration, wherein at least a portion of the second jaw tip is proximal to and overlaps the first jaw tip when the jaw structure is in the closed configuration, wherein the first jaw has a first jaw track and a first jaw suture slot, wherein the first jaw track has a first jaw track straight portion and a first jaw track curved portion, wherein the first jaw suture slot extends along an outer surface of the first jaw such that at least a portion of the first jaw suture slot faces away from the device, wherein the second jaw has a second jaw track and a second jaw suture slot, wherein the second jaw track has a second jaw track straight portion and a second jaw track curved portion, and wherein the second jaw suture slot extends along an outer surface of the second jaw such that at least a portion of the second jaw suture slot faces away from the device;
a suture holder slidably attachable to the first jaw and the second jaw, wherein the suture holder is slidable in the first and second jaw tracks, wherein when a suture is attached to the suture holder, the suture is slideable in the first jaw suture slot when the suture holder is in the first jaw track and is slideable in the second jaw suture slot when the suture holder is in the second jaw track, wherein the suture holder has a suture holder first tip, a suture holder second tip, an extension, and a suture holder spine having a spine longitudinal axis, wherein the suture holder first and second tips are configured to pierce tissue, wherein the extension extends away from the spine longitudinal axis and away from a surface of the first jaw track toward the outer surface of the first jaw when the suture holder is in the first jaw track, wherein the extension extends away from the spine longitudinal axis and away from a surface of the second jaw track toward the outer surface of the second jaw when the suture holder is in the second jaw track, wherein the extension is configured to limit movement of the suture holder when the suture holder is in the first jaw track or the second jaw track, wherein the first jaw suture slot exposes an outer surface of the suture holder when the suture holder is slidably attached to the first jaw, wherein the first jaw suture slot exposes a surface of the first jaw track when the suture holder is slidably attached to the second jaw, wherein the second jaw suture slot exposes the outer surface of the suture holder when the suture holder is slidably attached to the second jaw, and wherein the second jaw suture slot exposes a surface of the second jaw track when the suture holder is slidably attached to the first jaw;
a first pusher and a second pusher, wherein the first pusher is slidable in the first jaw track and the second pusher is slidable in the second jaw track, wherein the first pusher has a first pusher shuttle seat configured to contact the suture holder first tip, wherein the second pusher has a second pusher shuttle seat configured to contact the suture holder second tip, wherein the first pusher is configured to push the suture holder from the first jaw track to the second jaw track, wherein the second pusher is configured to push the suture holder from the second jaw track to the first jaw track, wherein when the device is in a closed first configuration, the first pusher is in an advanced position in the first jaw track and the second pusher is in a retracted position in the second jaw track, wherein when the device is in a closed second configuration, the first pusher is in a retracted position in the first jaw track and the second pusher is in an advanced position in the second jaw track;
an opening element between the first jaw and the second jaw, wherein the opening element is configured to produce an outward force against the first jaw when the opening element is translated in a first direction along the longitudinal axis of the jaw structure; and a compression cover configured to compress the first jaw toward the second jaw when the compression cover is translated with respect to the jaw structure against a first jaw compression cover surface and a second jaw compression cover surface, wherein when the jaw structure is in the closed configuration, the first jaw and second jaw compression cover surfaces are within the compression cover, and wherein when the jaw structure is in an open configuration, the first jaw and second jaw compression cover surfaces are outside of the compression cover, wherein the first jaw track terminates at a first jaw tip suture holder port and the second jaw track terminates at a second jaw tip suture holder port, wherein when the jaw structure is in the closed configuration, the first jaw tip contacts the second jaw tip, wherein when the jaw structure is in the closed configuration, the tooth and the tooth seat align the first jaw tip suture holder port and the second jaw tip suture holder port, wherein when the jaw structure is in the closed configuration, the first jaw tip suture holder port is in contact with the second jaw tip suture holder port, wherein when the jaw structure is in the closed configuration, the first and second jaw tracks form a continuous suture holder track, and wherein when the jaw structure in the closed configuration, the first jaw suture slot is aligned with the second jaw suture slot, wherein when the jaw structure is in an open first configuration, the suture holder is in the first jaw track and the suture holder first tip extends out of the first jaw tip suture holder port toward the second jaw, and wherein when the jaw structure is in an open second configuration, the suture holder is in the second jaw track and the suture holder second tip extends out of the second jaw tip suture holder port toward the first jaw.

2. The device of claim 1, wherein the opening element comprises a ball positioned in contact with the first jaw.

3. The device of claim 2, wherein the compression cover is slidable along the longitudinal axis of the jaw structure.

4. The device of claim 1, wherein the extension extends away from a first jaw track longitudinal axis toward the outer surface of the first jaw when the suture holder is in the first jaw track and extends away from a second jaw track longitudinal axis toward the outer surface of the second jaw when the suture holder is in the second jaw track, and wherein the extension extends into the first jaw suture slot when the suture holder is in the first jaw track and extends into the second jaw suture slot when the suture holder is in the second jaw track.

5. The device of claim 1, wherein the first jaw suture slot extends medially along the outer surface of the first jaw and the second jaw suture slot extends medially along the outer surface of the second jaw, wherein the first jaw track has a first jaw track longitudinal axis having a straight portion and a curved portion, wherein the second jaw track has a second jaw track longitudinal axis having a straight portion and a curved portion, and wherein the straight portion of the first jaw track longitudinal axis and the straight portion of the second jaw track longitudinal axis are at an angle relative to a longitudinal axis of the device when the device is in the closed configuration and when the device is in the open configuration.

6. The device of claim 1, wherein the suture holder has a suture holder first longitudinal end and a suture holder second longitudinal end, wherein the suture holder first longitudinal end has a shape of the first jaw track when the suture holder first longitudinal end is in the first jaw track, wherein the suture holder first longitudinal end has a shape of the second jaw track when the suture holder first longitudinal end is in the second jaw track, and wherein the suture holder first longitudinal end is straight when the suture holder first longitudinal end is in the first jaw track and is curved when the suture holder first longitudinal end is in the second jaw track.

7. The device of claim 1, wherein the first pusher has slots configured to increase a flexibility of the first pusher and wherein the second pusher has slots configured to increase a flexibility of the second pusher.

8. The device of claim 1, wherein the first pusher shuttle seat is configured to receive the suture holder first tip and the second pusher shuttle seat is configured to receive the suture holder second tip, wherein the first pusher shuttle seat is V-shaped or A-shaped, wherein the suture holder first tip is V-shaped or A-shaped, wherein the second pusher shuttle seat is V-shaped or A-shaped and wherein the suture holder second tip is V-shaped or A-shaped.

9. A suture manipulating device comprising:

a jaw structure having a longitudinal axis, wherein the jaw structure comprises a first jaw and a second jaw, wherein the first jaw has a first jaw tip and the second jaw has a second jaw tip, wherein the first jaw tip has a tissue cutter and the second jaw tip has a tissue cutter seat configured to contact the tissue cutter, wherein the tissue cutter is configured to interdigitate with the tissue cutter seat when the jaw structure is in a closed configuration, wherein at least a portion of the second jaw tip is proximal to and overlaps the first jaw tip when the jaw structure is in the closed configuration, wherein the first jaw has a first jaw track and a first jaw suture slot, wherein the first jaw track has a first jaw track straight portion and a first jaw track curved portion, wherein the first jaw suture slot extends along an outer surface of the first jaw such that at least a portion of the first jaw suture slot faces away from the device, wherein the second jaw has a second jaw track and a second jaw suture slot, wherein the second jaw track has a second jaw track straight portion and a second jaw track curved portion, and wherein the second jaw suture slot extends along an outer surface of the second jaw such that at least a portion of the second jaw suture slot faces away from the device;

a suture holder moveable in the first jaw and the second jaw, wherein the suture holder is moveable across a longitudinal axis of the device, wherein the suture holder is slidable in the first and second jaw tracks, wherein when a suture is attached to the suture holder, the suture is slideable in the first jaw suture slot when the suture holder is in the first jaw track and is slideable in the second jaw suture slot when the suture holder is in the second jaw track, wherein the suture holder has a suture holder first tip, a suture holder second tip, an extension, and a suture holder spine having a spine longitudinal axis, wherein the suture holder first and second tips are configured to cut tissue, wherein the extension extends away from the spine longitudinal axis toward a side of the first jaw track when the suture holder is in the first jaw track, wherein the extension extends away from the spine longitudinal axis toward a side of the second jaw track when the suture holder is in the second jaw track, wherein the extension is configured contact the first jaw when the suture holder is in the first jaw track and is configured to contact the second jaw when the suture holder is in the second jaw track, wherein the first jaw suture slot exposes an outer surface of the suture holder when the suture holder is in the first jaw, wherein the first jaw suture slot exposes a surface of the first jaw track when the suture holder is in the second jaw, wherein the second jaw suture slot exposes the outer surface of the suture holder when the suture holder is in the second jaw, and wherein the second jaw suture slot exposes a surface of the second jaw track when the suture holder is in the first jaw;

a first pusher and a second pusher, wherein the first pusher is slidable in the first jaw track and the second pusher is slidable in the second jaw track, wherein the first pusher has a first pusher shuttle seat configured to contact the suture holder first tip, wherein the second pusher has a second pusher shuttle seat configured to contact the suture holder second tip, wherein the first pusher is configured to push the suture holder from the first jaw track to the second jaw track, wherein the second pusher is configured to push the suture holder from the second jaw track to the first jaw track, wherein when the device is in a closed first configuration, the first pusher is in an advanced position in the first jaw track and the second pusher is in a retracted position in the second jaw track, wherein when the device is in a closed second configuration, the first pusher is in a retracted position in the first jaw track and the second pusher is in an advanced position in the second jaw track;

an opening element movable relative to the first jaw and the second jaw along the longitudinal axis of the device, wherein when the jaw structure is in the closed configuration, the opening element is configured to contact the first jaw and the second jaw at first and second jaw first locations, wherein when the jaw structure is in an open configuration, the opening element is configured to contact the first jaw and the second jaw at first and second jaw second locations proximal to the first and second jaw first locations; and a compression cover moveable relative to the first jaw and the second jaw along the longitudinal axis of the device, wherein the compression cover is configured to compress the first and second jaws toward the longitudinal axis of the device when the compression cover is moved relative to the jaw structure against a first jaw compression cover surface and a second jaw compression cover surface as the device changes configuration from the opening configuration to the closed configuration, wherein when the jaw structure is in the closed configuration, the first jaw and second jaw compression cover surfaces are within the compression cover, and wherein when the jaw structure is in an open configuration, the first jaw and second jaw compression cover surfaces are outside of the compression cover, wherein the first jaw track terminates at a first jaw tip suture holder port and the second jaw track terminates at a second jaw tip suture holder port, wherein when the jaw structure is in the closed configuration, the first jaw tip contacts the second jaw tip, wherein when the jaw structure is in the closed configuration, the tissue cutter and the tissue cutter seat align the first jaw tip suture holder port and the second jaw tip suture holder port, wherein when the jaw structure is in the closed configuration, the first jaw tip suture holder port is in contact with the second jaw tip suture holder port, wherein when the jaw structure is in the closed configuration, the first and second jaw tracks form a continuous suture holder track, and wherein when the jaw structure in the closed configuration, the first jaw suture slot is aligned with the second jaw suture slot, wherein when the jaw structure is in an open first configuration, the suture holder is in the first jaw track and the suture holder first tip extends out of the first jaw tip suture holder port toward the second jaw, and wherein when the jaw structure is in an open second configuration, the suture holder is in the second jaw track and the suture holder second tip extends out of the second jaw tip suture holder port toward the first jaw.

10. The device of claim 9, wherein the suture holder is attached to a flexible rail, and wherein the rail is slidably attached to the jaw structure, and wherein the rail is slidable along a longitudinal axis of the first jaw.

11. The device of claim 9, wherein the extension extends away from a first jaw track longitudinal axis toward the outer surface of the first jaw when the suture holder is in the first jaw track and extends away from a second jaw track longitudinal axis toward the outer surface of the second jaw when the suture holder is in the second jaw track, and
wherein the extension extends into the first jaw suture slot when the suture holder is in the first jaw track and extends into the second jaw suture slot when the suture holder is in the second jaw track.

12. The device of claim 9, wherein the first jaw suture slot extends medially along the outer surface of the first jaw and the second jaw suture slot extends medially along the outer surface of the second jaw,
wherein the first jaw track has a first jaw track longitudinal axis having a straight portion and a curved portion, wherein the second jaw track has a second jaw track longitudinal axis having a straight portion and a curved portion, and wherein the straight portion of the first jaw track longitudinal axis and the straight portion of the second jaw track longitudinal axis are at an angle relative to a longitudinal axis of the device when the device is in the closed configuration and when the device is in the open configuration.

13. The device of claim 9, wherein the suture holder has a suture holder first longitudinal end and a suture holder second longitudinal end, wherein the suture holder first longitudinal end has a shape of the first jaw track when the suture holder first longitudinal end is in the first jaw track, wherein the suture holder first longitudinal end has a shape of the second jaw track when the suture holder first longitudinal end is in the second jaw track, and
wherein the suture holder first longitudinal end is straight when the suture holder first longitudinal end is in the first jaw track and is curved when the suture holder first longitudinal end is in the second jaw track.

14. The device of claim 9, wherein the suture holder has slots configured to increase a flexibility of the suture holder.

15. The device of claim 9, wherein the first pusher shuttle seat is configured to receive the suture holder first tip and the second pusher shuttle seat is configured to receive the suture holder second tip, wherein the first pusher shuttle seat is V-shaped or A-shaped, wherein the suture holder first tip is V-shaped or A-shaped, wherein the second pusher shuttle seat is V-shaped or A-shaped and wherein the suture holder second tip is V-shaped or A-shaped.

16. A suture manipulating device comprising:
a jaw structure comprising a first jaw and a second jaw, and wherein the first jaw has a first jaw tip and wherein the second jaw has a second jaw tip, wherein the first jaw tip is configured to interdigitate with the second jaw tip, wherein a terminus of the first jaw and a terminus of the second jaw tip are sharpened, wherein the first jaw has a first jaw track and a first jaw suture slot, wherein the first jaw track has a first jaw track straight portion and a first jaw track curved portion, wherein the first jaw suture slot extends along an outer surface of the first jaw such that at least a portion of the first jaw suture slot faces away from the device, wherein the second jaw has a second jaw track and a second jaw suture slot, wherein the second jaw track has a second jaw track straight portion and a second jaw track curved portion, and wherein the second jaw suture slot extends along an outer surface of the second jaw such that at least a portion of the second jaw suture slot faces away from the device;

a suture holder slidably attachable to the first jaw and slidably attachable to the second jaw, wherein the suture holder is slidable in the first and second jaw tracks, wherein when a suture is attached to the suture holder, the suture is slideable in the first jaw suture slot when the suture holder is in the first jaw track and is slideable in the second jaw suture slot when the suture holder is in the second jaw track, wherein the suture holder has a suture holder first tip, a suture holder second tip, a first extension, a second extension, and a suture holder spine having a spine longitudinal axis, wherein the suture holder first and second tips are configured to pierce tissue, wherein the first and second extensions extend away from the spine longitudinal axis and away from a surface of the first jaw track toward the outer surface of the first jaw when the suture holder is in the first jaw track, wherein the first and second extensions extend away from the spine longitudinal axis and away from a surface of the second jaw track toward the outer surface of the second jaw when the suture holder is in the second jaw track, wherein the first extension is configured to limit movement of the suture holder when the suture holder is in the first jaw track, wherein the second extension is configured to limit movement of the suture holder when the suture holder is in the second jaw track, wherein the first jaw suture slot exposes an outer surface of the suture holder when the suture holder is in the first jaw, wherein the first jaw suture slot exposes a surface of the first jaw track when the suture holder is in the second jaw, wherein the second jaw suture slot exposes the outer surface of the suture holder when the suture holder is in the second jaw, and wherein the second jaw suture slot exposes a surface of the second jaw track when the suture holder is in the first jaw;

a first pusher and a second pusher, wherein the first pusher is slidable in the first jaw track and the second pusher is slidable in the second jaw track, wherein the first pusher has a first pusher shuttle seat configured to contact the suture holder first tip, wherein the second pusher has a second pusher shuttle seat configured to contact the suture holder second tip, wherein the first pusher is configured to push the suture holder from the first jaw track to the second jaw track, wherein the second pusher is configured to push the suture holder from the second jaw track to the first jaw track, wherein when the device is in a closed first configuration, the first pusher is in an advanced position in the first jaw track and the second pusher is in a retracted position in the second jaw track, wherein when the device is in a closed second configuration, the first pusher is in a retracted position in the first jaw track and the second pusher is in an advanced position in the second jaw track;

an opening element, wherein when the jaw structure is in the closed configuration, the opening element is configured to contact the first jaw at a first jaw first position and the second jaw at a second jaw first position, wherein when the jaw structure is in an open configuration, the opening element is configured to contact the first jaw at a first jaw second position and the second jaw at a second jaw second position, wherein the first and second jaw first positions are distal to the first and second jaw second locations along the longitudinal axis of the jaw structure; and a compression cover, wherein the compression cover is configured to apply a force against a first jaw compression cover surface and a second jaw compression cover surface as the device changes configuration from the opening configuration to the closed configuration, wherein when the jaw structure is in the closed configuration, the first jaw and second jaw compression cover surfaces are within the compression cover, and wherein when the jaw structure is in an open configuration, the first jaw and second jaw compression cover surfaces are outside of the compression cover, wherein the first jaw track terminates at a first jaw tip suture holder port and the second jaw track terminates at a second jaw tip suture holder port, wherein when the jaw structure is in the closed configuration, the first jaw tip contacts the second jaw tip, wherein when the jaw structure is in the closed configuration, the first jaw tip and the second jaw tip align the first jaw tip suture holder port and the second jaw tip suture holder port, wherein when the jaw structure is in the closed configuration, the first jaw tip suture holder port is in contact with the second jaw tip suture holder port, wherein when the jaw structure is in the closed configuration, the first and second jaw tracks form a continuous suture holder track, and wherein when the jaw structure in the closed configuration, the first jaw suture slot is aligned with the second jaw suture slot, wherein when the jaw structure is in an open first configuration, the suture holder is in the first jaw track and the suture holder first tip extends out of the first jaw tip suture holder port, and wherein when the jaw structure is in an open second configuration, the suture holder is in the second jaw track and the suture holder second tip extends out of the second jaw tip suture holder port.

17. The device of claim 16, wherein the first jaw suture slot extends medially along the outer surface of the first jaw and the second jaw suture slot extends medially along the outer surface of the second jaw, wherein the suture holder has a suture holder first longitudinal end and a suture holder second longitudinal end, wherein the suture holder first longitudinal end has a shape of the first jaw track when the suture holder first longitudinal end is in the first jaw track, wherein the suture holder first longitudinal end has a shape of the second jaw track when the suture holder first longitudinal end is in the second jaw track, and wherein the suture holder first longitudinal end is straight when the suture holder first longitudinal end is in the first jaw track and is curved when the suture holder first longitudinal end is in the second jaw track.

18. The device of claim 16, wherein the first jaw track has a first jaw track longitudinal axis having a straight portion and a curved portion, wherein the second jaw track has a second jaw track longitudinal axis having a straight portion and a curved portion, and wherein the straight portion of the first jaw track longitudinal axis and the straight portion of the second jaw track longitudinal axis are at an angle relative to a longitudinal axis of the device when the device is in the closed configuration and when the device is in the open configuration.

19. The device of claim 16, wherein the jaw structure and the opening element are longitudinally moveable relative to one another along a longitudinal axis of the device, and wherein the jaw structure and the compression cover are longitudinally moveable relative to one another along a longitudinal axis of the device.

20. The device of claim 16, wherein relative longitudinal movement between the jaw structure and the opening element is configured to open the jaw structure from the closed configuration to the open configuration and wherein relative longitudinal movement between the jaw structure and the compression cover is configured to close the jaw structure from the open configuration to the closed configuration.

* * * * *